(12) United States Patent
Wakita et al.

(10) Patent No.: US 8,993,228 B2
(45) Date of Patent: Mar. 31, 2015

(54) ANTIBODY BINDING TO ENVELOPE PROTEIN 2 OF HEPATITIS C VIRUS AND METHOD FOR IDENTIFYING GENOTYPE OF HEPATITIS C VIRUS USING THE SAME

(75) Inventors: Takaji Wakita, Tokyo (JP); Yuko Akazawa, Kanagawa (JP); Noriko Nakamura, Kanagawa (JP)

(73) Assignees: Toray Industries, Inc., Tokyo (JP); Japan as Represented by Director General of National Institute of Infectious Diseases, Tokyo (JP)

( * ) Notice: Subject to any disclaimer, the term of this patent is extended or adjusted under 35 U.S.C. 154(b) by 779 days.

(21) Appl. No.: 13/121,914

(22) PCT Filed: Sep. 30, 2009

(86) PCT No.: PCT/JP2009/067051
§ 371 (c)(1),
(2), (4) Date: Mar. 30, 2011

(87) PCT Pub. No.: WO2010/038789
PCT Pub. Date: Apr. 8, 2010

(65) Prior Publication Data
US 2011/0201014 A1 Aug. 18, 2011

(30) Foreign Application Priority Data

Sep. 30, 2008 (JP) ................................ 2008-254338

(51) Int. Cl.
*G01N 33/576* (2006.01)
*A61K 39/29* (2006.01)
*C07K 16/08* (2006.01)
*G01N 33/569* (2006.01)
*C07K 16/10* (2006.01)

(52) U.S. Cl.
CPC ........ *G01N 33/56983* (2013.01); *C07K 16/109* (2013.01); *C07K 2317/34* (2013.01); *G01N 2333/18* (2013.01)
USPC .............. 435/5; 435/7.1; 435/7.2; 435/70.21; 436/536

(58) Field of Classification Search
None
See application file for complete search history.

(56) References Cited

FOREIGN PATENT DOCUMENTS

| JP | 2008-517973 A | 5/2008 |
|---|---|---|
| WO | WO 92/13892 A1 | 8/1992 |
| WO | WO 99/50301 A2 | 10/1999 |
| WO | WO 00/26418 A1 | 5/2000 |
| WO | WO 02/055560 A2 | 7/2002 |
| WO | WO 2006/045677 A1 | 5/2006 |

OTHER PUBLICATIONS

Immune epitope database and analysis resource for Epitope ID: 67405, disclosed 1999.*
Campbell. Laboratory Techniques in Biochemistry and Molecular Biology. Monoclonal Antibody Technology. vol. 13. 1984. p. 1-33.*
Hiroishi et al. Cytotoxic T lymphocyte response and viral load in hepatitis C virus infection. Hepatology. Mar. 1997;25(3):705-12.*
Fried, M. et al. "Peginterferon ALFA-2a Plus Ribaviron for Chronic Hepatitis C Virus Infection", N. Engl. J. Med., 2002, vol. 347, p. 975-982.
Hadlock, K. et al. "Cross-Reactivity and Clinical Impact of the Antibody Response to Hepatitis C Virus Second Envelope Glycoprotein (E2)", Journal of Medical Virology, 2001, vol. 65, p. 23-29.
Hadlock, K. et al., "Human Monoclonal Antibodies That Inhibit Binding of Hepatitis C Virus E2 Protein to CD81 and Recognize Conserved Conformational Epitopes", J. of Virology, 2000, vol. 74, No. 22, p. 10407-10416.
International Search Report, dated Nov. 10, 2009, issued in PCT/JP2009/067051.
Lusida, M. et al. "Correlation between Mutations in the Interferon Sensitivity-Determining Region of NS5A Protein and Viral Load of Hepatitis C Virus Subtypes 1b, 1c, and 2a", J. Clin. Microbiol., 2001, vol. 39, p. 3858-3864.
Murakami, T. et al. "Mutations in Nonstructural Protein 5A Gene and Response to Interferon in Hepatitis C Virus Genotype 2 Infection", Hepatology, 1999, vol. 30, p. 1045-1053.
Okamoto, H. et al. "Typing hepatitis C virus by polymerase chain reaction with type-specific primers: application to clinical surveys and tracing infectious sources", J. Gen. Virol., 1992, vol. 73, p. 673-679.
Omi, N. et al. "Saibo Baiyokei ni yori Sansei sareta HCV Virus no Men'ekigensei ni Kansuru Kento" (Examination of Immunogenicity of HCV Virus Produced by Cell Culture System), The 55th Annual Meeting of the Japanese Society for Virology, 2007, p. 188.
Simmonds, P. et al. "A Proposed System for the Nomenclature of Hepatitis C Viral Genotypes", Hepatology, 1994, vol. 19, p. 1321-1324.

* cited by examiner

*Primary Examiner* — Michelle S Horning
(74) *Attorney, Agent, or Firm* — Birch, Stewart, Kolasch & Birch, LLP

(57) ABSTRACT

The present invention provides an antibody that specifically binds to envelope protein 2 of HCV of genotype 2*a* but does not immunologically react with envelope protein 2 of HCV of genotype 1*a*.

5 Claims, 9 Drawing Sheets

Figure 1:
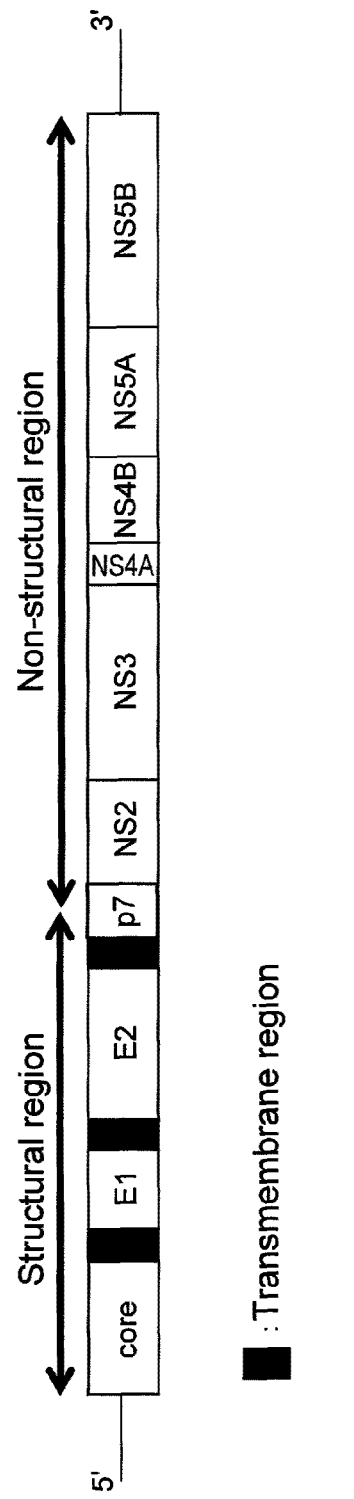

1. Molecular weight marker
2. Culture supernatant
3. Anti-FLAG antibody column Void fraction
4. Anti-FLAG antibody column elution fraction 1
5. Anti-FLAG antibody column elution fraction 2
6. Anti-FLAG antibody column elution fraction 3
7. Anti-FLAG antibody column elution fraction 4
8. Molecular weight marker 1. Molecular weight marker
2. J6E2-Fc
3. JFH1E2-Fc
4. THE2-Fc
5. Con1E2-Fc
6. J1E2-Fc
7. H77E2-Fc
8. Molecular weight marker

Fig. 6

| Clone name | HCV 2a | | HCV 1b | | | HCV 1a | Antibody subtype |
|---|---|---|---|---|---|---|---|
| | J6 | JFH1 | TH | Con1 | J1 | H77 | |
| 2F3-7 | +++ | +++ | +++ | +++ | +++ | + | IgG1/κ |
| 4E8-8 | +++ | +++ | +++ | +++ | +++ | - | IgG1/κ |
| 5D4-6 | +++ | +++ | +++ | + | +++ | - | IgG1/κ |
| 9G3-2 | +++ | ++ | - | +++ | +++ | - | IgG1/κ |
| 9A5-4 | +++ | +++ | - | - | - | +++ | IgG2b/κ |
| 9C4-2 | +++ | +++ | - | + | - | - | IgG2a/κ |
| 10G4-1 | +++ | +++ | - | +++ | +++ | - | IgG1/κ |
| 2F2-7 | ++ | +++ | - | - | - | - | IgG1/κ |
| 1G2-32 | +++ | +++ | - | - | - | - | IgG2a/κ |
| 8D10-3 | +++ | +++ | +++ | +++ | +++ | +++ | IgG1/κ |
| M1E12-1 | ++ | - | - | - | - | - | IgG1/κ |

OD450nm < 0.1　　　　-
0.1 ≦ OD450nm < 0.25　　+
0.25 ≦ OD450nm < 0.4　　++
0.4 ≦ OD450nm　　　　+++

ANTIBODY BINDING TO ENVELOPE PROTEIN 2 OF HEPATITIS C VIRUS AND METHOD FOR IDENTIFYING GENOTYPE OF HEPATITIS C VIRUS USING THE SAME

TECHNICAL FIELD

The present invention relates to an antibody binding to envelope protein 2 of Hepatitis C virus and a method for identifying the genotype of Hepatitis C virus using the antibody.

BACKGROUND ART

Hepatitis C virus (which may be also referred to as "HCV" hereinafter) is a major causative virus of non-A and non-B hepatitis, which infects mainly via transfusion and sexual contact (Choo et al., Science, Vol. 244: 359-362, 1989). It has been estimated that there are 2,000,000 or more HCV carriers in Japan including those who show no hepatitis symptoms (virus carriers), and there are 170,000,000 or more HCV carriers in the world. The major causes for the increasing number of HCV carriers are the fact that the chronicity rate of hepatitis due to HCV infection is as high as 70% to 80%, and the fact that effective antiviral agents other than interferons do not exist.

Pathological conditions exhibited by half or more of chronic hepatitis C patients will almost certainly go from bad to worse and are known to progress to cirrhosis or cancer of the liver. Hence, it can be said that hepatitis C is a serious infectious disease with a poor prognosis. Therefore, studies concerning the treatment of hepatitis C and the detection of HCV are medically important, and development of new therapies and therapeutic drugs has been desired.

HCV is a single-stranded (+) RNA virus having a genome length of approximately 9.6 kb, in which the genome encodes a precursor protein that is converted into 10 types of virus protein (i.e., Core, E1, E2, p7, NS2, NS3, NS4A, NS4B, NS5A, and NS5B proteins) via post-translational cleavage by host-derived signal peptidase or HCV-derived proteases. HCV is classified into 10 or more genotypes (e.g., 1a, 1b, 2a, 2b, 3a, and 3b) according to phylogenetic analysis of the nucleotide sequences of the genome (Choo et al., Science, 1989, Vol. 244, p. 359-362; Simmonds et al., Hepatology, 1994, Vol. 19, p. 1321-1324; Okamoto et al., J. Gen. Virol., 1992, Vol. 73, p. 73-679; and Mori et al., Biochem. Biophys. Res. Commun., 1992, Vol. 183, p. 334-342).

Recently, it has become known that the effects of interferons vary significantly depending on HCV genotype. It has been revealed that the antiviral action of interferons is exerted with difficulty on HCV of genotype 1a or 1b (Fried et al., N. Engl. J. Med., 2002, Vol. 347, p. 975-982 and Lusida et al., J. Clin. Microbiol., 2001, Vol. 39, p. 3858-3864).

Furthermore, it has become known that the antiviral action of interferons is exerted differently on HCV of genotype 2a and HCV of genotype 2b, on which interferons have relatively good effects. It has been suggested that interferons exert their antiviral action more significantly on HCV of genotype 2a than on HCV of genotype 2b (Murakami et al., Hepatology, 1999, Vol. 30, p. 1045-1053).

An HCV antibody test is known as an HCV diagnostic method by which an anti-HCV antibody in serum is detected using a C100-3 antigen, since the anti-HCV antibody recognizing the NS4 region (C100-3 antigen), which is a nonstructural region of HCV, exists at the rate of 70%-80% in the serum of a hepatitis C patient (Choo et al., Science, 1989, Vol. 244, p. 359-362). Also, as variations of this method, a second-generation antibody assay system with detection sensitivity that has been improved using a combination of the C100-3 antigen, a core antigen, and an antigen from the NS3 region and a third-generation antibody assay system also containing an antigen from the NS5 region in addition to the above antigens have been developed. HCV antibody tests using these assay systems have been used (Aucella et al., Blood Purif., 2000, Vol. 18, p. 110-114).

Also, other than the aforementioned HCV antibody tests, an HCV core antigen test (Fabrizi et al., J. Clin. Microbiol., 2005, Vol. 43, p. 414-420) is used for direct measurement of the amount of an HCV core protein in serum and a nucleic acid amplification test (NAT) is used for confirmation of the presence or absence of the HCV genome by a PCR method (Velati et al., Euro Serveill., 2005, Vol. 10, p. 12-14).

However, HCV antibody tests are problematic in that when a subject has experienced HCV infection in the past, the subject would unavoidably test positive for hepatitis C, even after being completely cured. HCV antibody tests are also problematic, since an anti-HCV antibody in blood is detected only when 1 to 3 months have passed after infection. If a test is conducted before such time, HCV cannot be detected and the subject would test negative for hepatitis C.

Also, HCV core antigen tests need treatment to cause the liberation of a core protein by disrupting the envelope using SDS, since the core protein (a target molecule) is present within HCV particles. Depending on treatment time with SDS, the core protein may be denatured or substances inhibiting the antigen-antibody reaction may be liberated, thus effecting detection sensitivity.

Furthermore, even when a subject tests positive for HCV in an HCV antibody test and an HCV core antigen test, it is currently impossible to identify the HCV genotype. To conduct interferon therapy, further tests, such as a nucleic acid amplification test, must be conducted in order to identify the HCV genotype. This is because the antiviral action of interferons significantly differs depending on HCV genotype. Particularly on HCV genotype 1a and HCV genotype 1b, effective antiviral action cannot be exerted, and patients rather suffer from adverse effects of interferon.

Meanwhile, a nucleic acid amplification test is problematic in relation to insufficient preservative quality and stability for test samples, since the test uses serum RNA of a subject as a target molecule. The nucleic acid amplification test also presents various problems, and precautions are necessary in regards to the use of an RT-PCR method. For example, PCR may be carried out after transcription of RNA as a target molecule to DNA, resulting in a false negative result due to RNA degradation or inactivation and/or inhibition of a reverse transcriptase or a false positive result due to cross contamination of a reaction system. Hence, the nucleic acid amplification test is thought to be inferior to an HCV antibody test or an HCV core antigen test using a protein as a target molecule in terms of accuracy.

DISCLOSURE OF THE INVENTION

Problem to be Solved by the Invention

Objects of the present invention are to provide antibodies that bind to envelopes on HCV surfaces and can be used for identifying HCV of genotype 1a, HCV of genotype 1b, and HCV of genotype 2a and to provide a method for identifying HCV genotypes using such antibodies.

Means for Solving the Problem

The present inventors conducted concentrated studies in order to achieve the above objects. They obtained hybridomas producing monoclonal antibodies against envelope protein 2 of HCV genotype 2a as an antigen, obtained from among the hybridomas, an antibody specifically binding to only envelope protein 2 of HCV genotype 2a, an antibody binding to only envelope protein 2 of HCV genotype 2a and envelope protein 2 of HCV genotype 1b, and an antibody binding to envelope protein 2 of HCV genotype 2a, envelope protein 2 of HCV genotype 1b, and envelope protein 2 of HCV genotype 1a, and thus they completed the present invention.

Specifically, the present invention provides an antibody that specifically binds to envelope protein 2 of HCV of genotype 2a but does not immunologically react with envelope protein 2 of HCV of genotype 1a.

The above antibody is preferably an antibody that recognizes the amino acid sequence shown in SEQ ID NO: 1 in the Sequence Listing as an epitope. An example of such an antibody is an antibody that is produced by the hybridoma cell line having accession No. FERM BP-11181.

Also, preferably the above antibody specifically binds to envelope protein 2 of HCV of genotype 2a, but it does not immunologically react with envelope protein 2 of HCV of genotype 1a and envelope protein 2 of HCV of genotype 1b.

The above antibody is more preferably an antibody that recognizes the amino acid sequence shown in SEQ ID NO: 2 or 3 in the Sequence Listing as an epitope. An example of such an antibody is an antibody that is produced by the hybridoma cell line having accession No. FERM BP-11180 or FERM BP-11179.

Moreover, the above antibody is preferably an antibody that specifically binds to envelope protein 2 of the J6CF strain but does not immunologically react with envelope protein 2 of the JFH1 strain. Examples of such an antibody include an antibody that recognizes the amino acid sequence shown in SEQ ID NO: 4 in the Sequence Listing as an epitope, in particular, an antibody that is produced by the hybridoma cell line having accession No. FERM BP-11183.

Also, the present invention provides a method for identifying HCV genotypes, wherein: the genotype of HCV is determined to be genotype l*b* if the virus binds to the antibody that is produced by the hybridoma cell line having accession No. FERM BP-11181 but does not bind to either of antibodies that are produced by the hybridoma cell lines having accession Nos. FERM BP-11180 and FERM BP-11179; the genotype of HCV is determined to be genotype 2*a* if the virus binds to an antibody that is produced by the hybridoma cell line having accession No. FERM BP-11181 and binds to the antibodies that are produced by the hybridoma cell lines having accession Nos. FERM BP-11180 and FERM BP-11179: and the genotype of HCV is determined to be genotype 1 *a* if the virus binds to an antibody that is produced by the hybridoma cell line having accession No. FERM BP-11182 but does not bind to any of antibodies that are produced by the hybridoma cell lines having accession Nos. FERM BP-11181, FERM BP-11180, and FERM BP-11179.

This description includes the contents of the description and/or drawings of Japanese Patent Application No. 2008-254338, to which the present application claims the priority.

Effects of the Invention

According to the present invention, simple and very accurate identification of HCV genotype 1a, HCV genotype 1b, and HCV genotype 2a is made possible and hepatitis C patients for whom interferon therapy is appropriate can be efficiently selected. In particular, adverse reactions can be alleviated and the chance of selecting a new therapeutic method can be provided for hepatitis C patients infected with HCV of genotype 1a or 1b, for which no therapeutic effects can be expected from interferon therapy.

BRIEF DESCRIPTION OF THE DRAWINGS

FIG. 1 is a schematic diagram showing an HCV precursor protein. Black squares indicate transmembrane regions.

FIG. 2 is a schematic diagram showing a fusion protein of a 3xFLAG protein and an antigen E2 protein.

FIG. 3 is a schematic diagram showing a fusion protein of an antigen E2 protein and a human immunoglobulin Fc domain.

FIG. 4 shows SDS-PAGE results for each fraction obtained in a step of purification of a 3xFLAGJ6E2dTM protein. Expression and purification of 3xFLAG-J6E2dTM in COS1 cells are shown. 3xFLAGJ6E2dTM protein was detected in an elution fraction. The lanes of the electrophoretic photograph in FIG. 4 indicate the following, respectively: 1, molecular weight marker; 2, culture supernatant; 3, anti-FLAG antibody column Void fraction; 4, anti-FLAG antibody column elution fraction 1; 5, anti-FLAG antibody column elution fraction 2; 6, anti-FLAG antibody column elution fraction 3; 7, anti-FLAG antibody column elution fraction 4; and 8, molecular weight marker.

FIG. 5 shows SDS-PAGE results for J6E2-Fc, JFH1E2-Fc, THE2-Fc, Con1E2-Fc, J1E2-Fc, and H77E2-Fc proteins. Each type of E2 Fc protein has approximately 97 kDa under reductive conditions. The purified fusion protein of each of HCV strain-derived antigen E2 proteins and a human immunoglobulin Fc domain is shown. The lanes of the electrophoretic photograph in FIG. 5 indicate the following, respectively: 1, molecular weight marker; 2, J6E2-Fc; 3, JFH1E2-Fc; 4, THE2-Fc; 5, Con1E2-Fc; 6, J1E2-Fc; 7, H77E2-Fc; and 8, molecular weight marker.

FIG. 6 shows the binding property to E2 proteins of various HCV genotypes/strains and antibody subtype of each monoclonal antibody. The strength of binding of an antibody to an antigen E2 protein is indicated with −to +++ (−, OD450 nm <0.1;+,0.1≤OD450 nm<0.25; ++, 0.25≤0D450 nm <0.4; +++, 0.4<OD450 nm). FIG. 6 indicates that: 8D10-3 is an antibody binding to the antigen E2 proteins of HCV of genotype l*a* and of HCV of genotype l*b*, and of HCV of genotype 2*a*; 1G2-32 and 2F2-7 are antibodies binding to the antigen E2 protein of HCV of genotype 2*a*; 4E8-8 is an antibody binding to the antigen E2 proteins of HCV of genotype l*b* and of HCV of genotype 2*a*; M1E12-1 is a monoclonal antibody binding to the antigen E2 protein of the J6CF strain; and 9A5-4 is a monoclonal antibody binding to the antigen E2 proteins of the J6CF strain and of the H77 strain.

FIG. 7 shows the binding strength of a 8D10-3 monoclonal antibody (FIG. 7A), a 1G2-32 monoclonal antibody (FIG. 7B), a 4E8-8 monoclonal antibody (FIG. 7C), a 2F2-7 monoclonal antibody (FIG. 7D), and a M1E12-1 monoclonal antibody (FIG. 7E) to peptides having amino acid sequences derived from the antigen E2 protein of the HCV J6CF strain.

FIG. 8 shows the sensitivity of detecting antigen E2 proteins derived from various HCV genotypes/HCV strains, as determined by sandwich ELISA using 1G2-32 and 8D10-3 monoclonal antibodies. In FIG. 8, the black circle indicates J6E2-Fc, the white circle indicates JFH1E2-Fc, the black square indicates THE2-Fc, the white square indicates Con1E2-Fc, the black diamond indicates J1E2-Fc, and the white diamond indicates H77E2-Fc.

FIG. 9 shows the presence or absence of HCVE2 proteins of various genotypes/strains as detected by a Western blot method using the monoclonal antibody 8D10-3.

MODES FOR CARRYING OUT THE INVENTION

Hereinafter, preferred embodiments for implementing the present invention will be described as follows.

The antibody of the present invention is characterized by specifically binding to envelope protein 2 (hereinafter, E2 protein) of HCV of genotype 2a (hereinafter, HCV2a), but not immunologically reacting with the E2 protein of HCV of genotype 1a (hereinafter, HCV1a). In a preferred embodiment, such an antibody does not immunologically react with both the E2 protein of HCV1a and the E2 protein of HCV of genotype 1b (hereinafter, HCV1b).

The above antibody can be prepared by immunizing an animal with an antigen protein consisting of the region without transmembrane region (also referred to as transmembrane domain) of an E2 protein of HCV or a partial peptide of the antigen protein as an antigen, preparing hybridomas producing monoclonal antibodies against the E2 protein, and then screening for hybridomas producing an antibody that specifically binds to the E2 protein of HCV2a but does not immunologically react with the E2 protein of HCV1a, and furthermore preferably does not immunologically react with both the E2 protein of HCV1a and the E2 protein of HCV1b.

Herein "E2 protein" is a functional virus protein generated via cleavage of an HCV precursor protein by host cell-derived signal peptidase and 2 types of protease encoded by HCV itself. This is explained using the J6CF strain of HCV2a as an example such that when methionine located at the N-terminus of a precursor protein is determined to be the $1^{st}$ amino acid, the E2 protein is a protein of 367 amino acids residues ranging from the amino acid positions 384 to 750 of the precursor protein. A region in the E2 protein, ranging from the amino acid positions 722 to 750, is a transmembrane domain (Cocquerel et al., J. Virol., 2000, Vol. 74, p. 3623-3633). FIG. 1 is a schematic diagram showing an HCV precursor protein.

Hereinafter, techniques for obtaining the above antibodies will be described sequentially.

1) Selection of E2 Protein-Derived Protein or Peptide as an Antigen

As an antigen to be used for immunization of an animal to obtain the above antibody, a protein consisting of the region without the transmembrane region from the E2 protein of HCV2a (hereinafter, antigen E2 protein) or a partial peptide of the protein (antigen E2 peptide) can be used. An antigen E2 peptide is required to consist of a region with low homology with the E2 protein of HCV of a genotype other than 2a.

As the antigen E2 protein, a protein comprising amino acids 384 to 720 of a precursor protein of HCV2a (e.g., SEQ ID NO: 5) may be selected. Preferably, a protein comprising the amino acid sequence ranging from amino acid positions 530 to 562 of the precursor protein is selected, and more preferably a protein comprising one or more amino acid sequences selected from the group consisting of: the amino acid sequence comprising amino acids 465 to 484; the amino acid sequence comprising amino acids 559 to 584 and the amino acid sequence comprising amino acids 683 to 719 of the precursor protein is selected.

Also, as the antigen E2 peptide, a peptide comprising amino acids 530 to 562 (more preferably, amino acids 531 to 549, and further preferably, amino acids 531 to 540) of a precursor protein of HCV2a (e.g., SEQ ID NO: 5) and having a peptide length of 10 to 19 amino acids (more preferably, 10 amino acids) may be selected. More preferably, a peptide comprising amino acids 465 to 484 (more preferably, amino acids 465 to 477 and further preferably amino acids 468 to 477) of the precursor protein and having a peptide length of 10 to 13 amino acids (more preferably, 10 amino acids); a peptide comprising amino acids 559 to 584 (more preferably, amino acids 564 to 576 and further preferably amino acids residues at positions 567 to 576) of the precursor protein and having a peptide length of 10 to 13 amino acids (more preferably, 0.10 amino acids); or a peptide comprising amino acids 683 to 719 (preferably, amino acids 704 to 719 and more preferably amino acids 709 to 719) of the precursor protein and having a peptide length of 10 to 19 amino acids (more preferably, 10 amino acids) is selected.

In addition, the nucleotide sequence of the HCV2a genome has already been revealed in many viral strains (Yanagi et al., Virology, 1999, Vol. 262, p. 250-263) and is available from GenBank. For example, the nucleotide sequence of the genome of the JFH1 strain of HCV2a is disclosed in GenBank under accession No. AB047639 and the nucleotide sequence of the genome of the J6CF strain is disclosed in GenBank under accession No. AF177036.

2) Preparation of Antigen E2 Peptides

The above selected antigen E2 peptides can be directly chemically synthesized based on the amino acid sequence information of the precursor protein of HCV2a. For example, such an antigen that can be used for immunization of animals can be easily prepared in a large amount by using a peptide synthesizer.

3) Preparation of Antigen E2 Protein

The above selected antigen E2 protein can be prepared in a large amount as an antigen that can be used for immunization of animals by synthesizing a DNA fragment encoding the antigen E2 protein based on the nucleotide sequence information concerning the region encoding the precursor protein of HCV2a and then causing the translation of the antigen E2 protein from the thus obtained DNA fragment in cells. This will be more specifically described as follows.

The antigen E2 protein can be produced in cells by constructing an expression vector in which a DNA fragment encoding the antigen E2 protein has been inserted and then carrying out transduction into mammalian cells, insect cells, yeast, *Escherichia coli*, or the like. Preferably the protein is produced via secretory expression by mammalian cells. In this case, a DNA fragment encoding an antigen E2 peptide is ligated in-frame downstream of the signal peptide sequence so that the frames of codon match, and a stop codon is added to the 3' terminus, and then the resultant may be inserted into an expression vector.

Examples of mammalian cells for secretory expression of an antigen E2 protein include, COS-1, COS-7, Vero, CV-1, CHO, dhfr gene-deficient CHO, hamster cell BHK, rat GH3, rat phaeochromocytoma PC12, mouse L cells, mouse C127 cells, mouse myeloma cells SP2/0, NSO, and NS-1, mouse lymphoma cells EL4, mouse fibroblasts NIH3T3 and 10T1/2, mouse myoblasts C2C12, mouse stromal cells PA6, ST2, OP9, and Tst-4, human megakaryoblastic cells CMK, human T cells Jurkat, human renal epithelial cells 293, human hepatic cancer cells Huh7, HepG2, and IMY-N9, human osteosarcoma cells MG-63, human FL cells, white adipocytes, ovum cells, and ES cells.

DNA encoding the protein is inserted under control of a promoter and then used for recombinant expression of an antigen E2 protein in cells. Examples of such a promoter that can be used for recombinant expression of an antigen E2 protein in mammalian cells include an SRα promoter, an SV40 promoter, an LTR promoter, a CMV promoter, an actin promoter, an EF-1a (elongation factor-1α) promoter, an ubiquitin promoter, and a PGK (phosphoglycerate kinase) promoter.

Examples of an expression vector for secretory expression of an antigen E2 protein in mammalian cells include pSecTag/

FRT/V5-His (Invitrogen Corporation), p3xFLAG-CMV-9 (Sigma), p3xFLAG-CMV13 (Sigma), pFUSE-Fc2 (InvivoGen), and pTriEx-7 (Novagen). A signal peptide sequence incorporated in an expression vector is preferably a signal peptide of preprotrypsin. Examples of a vector having the signal peptide sequence of preprotrypsin include p3xFLAG-CMV-9 (Sigma) and p3xFLAG-CMV-13 (Sigma). In addition, since when a protein containing a signal peptide is expressed in mammalian cells, the signal peptide is removed, such a signal peptide poses no problem upon the use of an antigen E2 protein.

Upon secretory expression of an antigen E2 protein in mammalian cells, the target antigen E2 protein is expressed as a fusion protein with a labeling protein (e.g., Tag) and then the antigen E2 protein can be detected and purified using an antibody against or a molecule specifically binding to the labeling protein. Examples of a labeling protein include a FLAG peptide, a 3xFLAG peptide, an HA peptide, a 3xHA peptide, an myc peptide, a 6xHis peptide, a GST polypeptide, an MBP polypeptide, a PDZ domain polypeptide, alkaline phosphatase, an immunoglobulin Fc domain, and avidin. As labeling proteins to be used for preparing an antigen E2 protein, a FLAG peptide, an HA peptide, and an immunoglobulin Fc domain are suitable and an immunoglobulin Fc domain is more suitable.

Figure 2:
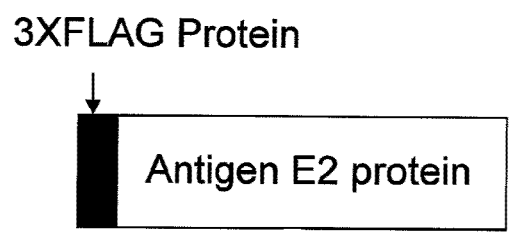
Figure 3:
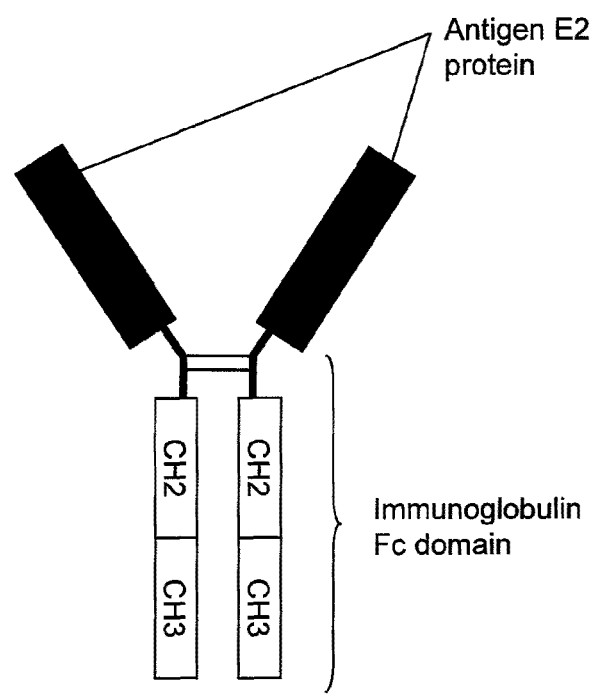

FIG. 2 is a schematic diagram showing a fusion protein of an antigen E2 protein and a 3xFLAG protein. FIG. 3 is a schematic diagram showing a fusion protein of an antigen E2 protein and an immunoglobulin Fc domain.

As such an immunoglobulin Fc domain, human-derived, monkey-derived, mouse-derived, rat-derived, rabbit-derived, hamster-derived, or chicken-derived immunoglobulin Fc domain can be used and a human-derived immunoglobulin Fc domain is preferred. In addition, the class of an immunoglobulin heavy chain of the immunoglobulin Fc domain may be IgM, IgG1, IgG2, IgG3, or IgG4.

The amino acid sequences of human immunoglobulins are as reported by Edelman et al. (Proc. Natl. Acad. Sci. U.S.A., 1969, Vol. 63, p. 78-85). Also, the nucleotide sequence information of the cDNAs of human immunoglobulin heavy chains is available from GenBank (the heavy chain: accession No. BX640627, for example). PCR primers are designed based on the obtained nucleotide sequences and then PCR is carried out using a cDNA library of human spleen cells or human genomic DNA as a template, so that the cDNA of the immunoglobulin Fc domain can be cloned.

An HCV E2 protein can be directly ligated to an immunoglobulin Fc domain at a connection site between them, or linked to it via a linker peptide inserted therein. Examples of a linker peptide include Ser-Gly, Asp-Pro, Asp-Pro-Glu, Gly-Asp-Pro-Glu, Gly-Gly-Gly-Ser, and (Gly-Gly-Gly-Ser)x3.

In addition, upon secretory expression of an antigen E2 protein by insect cells, for example, insect cells such as Sf21, Sf9, and High Five™ were transduced with an expression vector using a polyhedrin (polyhedral body) promoter, a p10 promoter, or the like. Then the antigen E2 protein or a fusion protein of the antigen E2 protein and a labeling protein may be expressed.

Also, upon secretory expression of an antigen E2 protein by yeast, for example, Saccharomyces cerevisiae, Schizosaccharomyces pombe, or Pichia pastoris is transduced with an expression vector using a gal1 promoter, a gal10 promoter, a heat shock protein promoter, an MFα1 promoter, a PHO5 promoter, a PGK promoter, a GAP promoter, an ADH promoter, an AOX1 promoter, or the like and then the antigen E2 protein or a fusion protein of the antigen E2 protein and a labeling protein may be expressed.

Upon secretory expression of an antigen E2 protein by Escherichia coli, for example, an Escherichia coli strain such as the XL1-Blue strain, the BL-21 strain, the JM107 strain, the TB1 strain, the JM109 strain, the C600 strain, or the HB101 strain is transformed with an expression vector using a trp promoter, a lac promoter, a PL promoter, a T7 promoter, a tac promoter, or the like and then the antigen E2 protein or a fusion protein of the antigen E2 protein and a labeling protein may be expressed.

Examples of a method for transduction with an expression vector in order to cause the secretory expression of an antigen E2 protein by mammalian cells and insect cells include a lipofection method, a calcium phosphate method, an electroporation method, a DEAE-dextran method, and a microinjection method. More specifically, transduction can be carried out according to the method described in Molecular Cloning $3^{rd}$. Ed. 16.1-16.62 (Cold Spring Harbor Laboratory, New York, 2001).

A method for introducing an expression vector into Escherichia coli is not particularly limited, as long as it is a method for introducing DNA into Escherichia coli. Examples of such a method include a method using calcium ions (Cohen et al., Proc. Natl. Acad. Sci., U.S.A., 1972, Vol. 69, p. 2110-2114) and an electroporation method.

A method for introducing an expression vector into yeast is not particularly limited, as long as it is a method for introducing DNA into yeast. Examples of such a method include an electroporation method (Becker et al., Methods. Enzymol., 1990, Vol. 194, p. 182-187), a spheroplast method (Hinnen et al., Proc. Natl. Acad. Sci., U.S.A., 1978, Vol. 75, p. 1929-1933), and a lithium acetate method (Itoh et al., J. Bacteriol., 1983, Vol. 153, p. 163-168).

Transduced cells may be cultured by a method known per se. As medium for culturing mammalian cells, for example, MEM medium, DMEM medium, RPMI 1640 medium, 199 medium (Proceeding of the Society for the Biological Medicine, 1950, Vol. 73, p. 1), containing about 5%-20% fetal bovine serum (FBS), or the like is used. The pH preferably ranges from about 6 to 8. As serum-free medium, CD-CHO, 293 SFM-II, and Hybridoma-SFM (these are all produced by Invitrogen Corporation) can be used and serum or a supplement may be added thereto as required. Cells may be cultured at 30° C. to 40° C. for 15 hours to 60 hours and aeration or agitation is preferably carried out as required.

After completion of cell culture, cells are removed from a culture solution by centrifugation or the like and then an antigen E2 protein or a fusion protein of the antigen E2 protein and a labeling protein can be purified from the thus obtained culture supernatant. The antigen E2 protein or the fusion protein of the antigen E2 protein and the labeling protein may be purified according to protein separation and purification techniques known by persons skilled in the art. For example, a protein can be isolated and purified by a combination of any of ammonium sulfate precipitation, gel chromatography, ion exchange chromatography, affinity chromatography, and the like.

For example, an antigen E2 protein in a culture solution can be easily purified using a heparin column or a lectin column. In the case of a fusion protein with a 3xFLAG peptide, the antigen E2 protein can be efficiently purified using an anti-FLAG antibody column, in the case of a fusion protein with an 6xHis peptide, the antigen E2 protein can be efficiently purified using a nickel column, a zinc column, or a cobalt column, in the case of a fusion protein with an immunoglobulin Fc domain, the antigen E2 protein can be efficiently purified using a protein A column or a protein G column, and in the case of a chimeric protein containing an HA peptide, the antigen E2 protein can be efficiently purified using an anti-HA antibody column.

The thus purified antigen E2 protein or fusion protein of the antigen E2 protein and the labeling protein can be detected by Coomassie brilliant blue staining or silver staining after SDS-PAGE fractionation. In the case of the fusion protein, the fusion protein can be detected by a Western blot method using an antibody against the fused labeling protein.

4) Immunization Using Antigen E2 Peptide or Antigen E2 Protein

To obtain an antibody that specifically binds to the E2 protein of HCV2a, but does not immunologically react with the E2 protein of HCV1a more preferably does not immunologically react with both the E2 protein of HCV1a and the E2 protein of HCV1b, immunization of animals using the above antigen E2 peptide or antigen E2 protein and then obtaining a polyclonal antibody or screening for hybridomas producing a monoclonal antibody of interest should be carried out.

Animals to be immunized may be non-human animals having spleen cells capable of being used for producing hybridoma cells. Examples of such an animal include mice, rats, hamsters, rabbits, and chickens. Mice can be more preferably used.

An example of a method for immunization comprises administering several times the above antigen E2 peptide or antigen E2 protein together with an adjuvant subcutaneously or intraperitoneally to 4- to 10-week-old mice, confirming an increase in blood antibody titer, boosting via intravenous or intraperitoneal administration of the antigen E2 peptide or antigen E2 protein alone, and then collecting blood or spleen cells on days 3 to 10 (preferably on day 4). The antibody titer of the serum obtained from the collected blood is measured. In this case, if it specifically recognizes the target antigen, it can be used as polyclonal antibodies.

Examples of an adjuvant include Freund's complete adjuvant, Freund's incomplete adjuvant, a mixture of aluminium hydroxide gel and a pertussis vaccine, Titer Max Gold (Vaxel), and GERBU adjuvant (GERBU Biotechnik).

The antibody titer in the blood is measured by collecting blood from an immunized animal via fundus venous plexus or tail vein and then examining by enzyme immunoassay (EIA) the presence or absence of an antibody reacting with an antigen E2 peptide or an antigen E2 protein in the obtained blood.

5) Preparation of Hybridoma Cells

Spleen cells collected from an immunized animal on days 3-10 after boosting, in which an increased antibody titer in the blood has been confirmed, are fused to myeloma cells, so that hybridoma cells having autonomous replicability can be prepared. A monoclonal antibody can be prepared in a large amount by screening for hybridoma cells producing an antibody having a target specificity.

As myeloma cells to be used for cell fusion, for example, mouse-derived established cell lines, P3-X63Ag8-U1 (P3-U1), SP2/0-Ag14 (SP2/0), P3-X63-Ag8653 (653), P3-X63-Ag8 (X63), P3/NS1/1-Ag4-1(NS1), and the like can be used. These cell lines are available from RIKEN BioResource Center, ATCC (American Type Culture Collection), or ECACC (European Collection of Cell Cultures).

Cell fusion of spleen cells and myeloma cells is carried out by washing both cells, mixing myeloma cells with spleen cells at a ratio of 1:1-10, and then adding polyethylene glycol or polyvinyl alcohol with an average molecular weight of 1000-6000 as a fusion accelerator or using a commercial cell fusion apparatus using electrical stimulation (e.g., electroporation).

After completion of treatment for cell fusion, fused cells are suspended in and washed with culture medium and then cloned by limiting dilution or a colony formation method in methylcellulose medium. An example of limiting dilution is a method that comprises diluting to $10^3$ to $10^7$ cells/mL, seeding the cells into a 96-well cell culture microplate at $10^2$ to $10^6$ cells/well, and then culturing the cells.

A HAT supplement is preferably added to culture medium when cloning of hybridoma cells is carried out, so as to be able to selectively obtain target fusion cells alone. More specifically, according to methods described in Antibodies: A Laboratory Manual (Cold Spring Harbor Laboratory, 1988) or Selected Methods in Cellular Immunology (W.H. Freeman and Company, 1980), hybridoma cells of interest are obtained and cloned.

6) Screening for Hybridoma Cell

Hybridoma cells of interest are screened for by an EIA method described below, for example.

Specifically, first, an antigen E2 peptide or an antigen E2 protein is immobilized on a carrier, an antibody produced by each cloned hybridoma cell is added to react for a time sufficient for the formation of an antibody-antigen complex under conditions of 4° C.-37° C.

Next, a secondary antibody labeled with an enzyme, a dye, a radioisotope, or the like and capable of specifically binding to an antibody portion of the thus formed antibody-antigen complex is contacted with the formed antibody-antigen complex to react for a time sufficient for the formation of an antibody-antigen-secondary antibody complex under conditions of 4° C.-37° C.

Finally, the presence or absence of the thus formed antibody-antigen-secondary antibody complex is detected using signals from an enzyme, a dye, or a radioisotope used for labeling the secondary antibody as an indicator, thereby determining if it is an antibody having target properties.

7) Preparation of Monoclonal Antibody

Hybridoma cells selected by the above method are conditioned to serum-free medium, e.g., Hybridoma-SFM (Invitrogen Corporation) and then a monoclonal antibody can be prepared from the supernatant from the culture in serum-free medium. For culturing cells, flasks, petri dishes, spinner culture bottles, roller bottles, or high density culture flasks CEL-Line (Becton, Dickinson and Company) can be used.

Also, in order to prepare a monoclonal antibody in a large amount, for example, 6- to 8-week-old nude mice or SCID mice may be administered intraperitoneally with 0.5 mL of pristane (2,6,10,14-tetramethylpentadecane), raised for 2 weeks, and then administered intraperitoneally with hybridoma cells at $5 \times 10^6$ to $2 \times 10^7$ cells/mouse and raised for 10 to 21 days, so that a monoclonal antibody can be prepared from the resulting ascites.

Cells and cellular debris are removed from the thus collected ascites by centrifugation. Purification means such as salting-out using 40%-50% saturated ammonium sulfate, a caprylic acid precipitation method, a DEAE-sepharose column, a protein A-column, a protein G-column, a HiTrap IgM Purification HP-column (GE Healthcare), a mannan binding protein-column (Pierce), and a gel filtration column are used alone or in combination, so that an IgG or IgM fraction is collected and then can be used as a purified monoclonal antibody.

8) Analysis of Epitope for Monoclonal Antibody

A linear epitope for a monoclonal antibody can be analyzed by synthesizing peptides that have amino acid sequences of 8 to 12 contiguous amino acids which were designed to be shifted by one to several amino acids in an antigen E2 protein, examining to which peptide a monoclonal antibody binds when the peptide is used as an antigen, and then determining an epitope for the antibody.

Specifically, the thus synthesized peptides are immobilized on a plate and reacted with a purified antibody. A labeled secondary antibody is added and then the plate is left to stand. The binding ability is measured by enzyme immunoassay (ELISA) or radioimmunoassay (RIA).

An epitope may not be determined by this method in some cases. In such cases, an epitope for a monoclonal antibody can be a conformation epitope and therefore the antibody may recognize the conformation of the antigen.

An example of an antibody that specifically binding to the E2 protein of HCV2a, but not immunologically reacting with the E2 protein of HCV1a is an antibody recognizing the amino acid sequence shown in SEQ ID NO: 1 in the Sequence Listing as an epitope. A specific example of such an antibody is an antibody that is produced from the hybridoma cell line having accession No. FERM BP-11181.

Also, an example of an antibody specifically binding to the E2 protein of HCV2a, but not immunologically reacting with both the E2 protein of HCV1a and the E2 protein of HCV1b is an antibody recognizing the amino acid sequence shown in SEQ ID NO: 2 or 3 in the Sequence Listing as an epitope. A specific example of such an antibody is an antibody that is produced by the hybridoma cell line having accession No. FERM BP-11180 or FERM BP-11179.

Moreover, an example of an antibody specifically binding to envelope protein 2 of the J6CF strain of HCV2a, but not immunologically reacting with envelope protein 2 of the JFH1 strain is an antibody recognizing the amino acid sequence shown in SEQ ID NO: 4 in the Sequence Listing as an epitope. A more specific example of such an antibody is an antibody that is produced by the hybridoma cell line having accession No. FERM BP-11183. This antibody can distinguish the J6CF strain from among HCV genotype 2a, so that it can be used for identifying the J6CF strain.

In addition, the above hybridoma cell lines having accession Nos. FERM BP-11181, FERM BP-11180, FERM BP-11179, FERM BP-11183, and FERM BP-11182 have been deposited with the international Depositary Authority, the International Patent Organism Depositary, National Institute of Advanced Industrial Science and Technology (postal code: 305-8566 Central 6, 1-1-1 Higashi, Tstikuba, Ibaraki, Japan) (deposition date: Sep. 19, 2008) and thus they are available. These cell lines were each originally deposited domestically (date of original deposition: Sep. 19, 2008) with the same depositary authority under accession Nos. FERM P-21677 (provisional accession No. FERM AP-21677), FERM P-21676 (provisional accession No. FERM AP-21676), FERM P-21675 (provisional accession No. FERM AP-21675), FERN P-21679 (provisional accession No. FERM AP-21679), and FERM P-21678 (provisional accession No. FERM AP-21678) and then transferred to international deposition under the Budapest Treaty.

Also, the method for identifying HCV genotypes of the present invention comprising: determining the genotype of HCV to be genotype 1b if the HCV binds to the antibody produced by the hybridoma cell line having accession No, FERM BP-11181 but does not bind to either of antibodies produced by the hybridoma cell lines having accession Nos. FERM BP-11180 and FERM BP-11179; determining the genotype of HCV to be genotype 2a if the HCV binds to the antibody produced by the hybridoma cell line having accession No. FERM BP-11181 and binds to the antibodies produced by the hybridoma cell lines having accession Nos. FERM BP-11180 and FERM BP-11179; and determining the genotype of HCV to be genotype 1a if the HCV binds to the antibody produced by the hybridoma cell line having accession No. FERM BP-11182, but does not bind to any of antibodies produced by the hybridoma cell lines having accession Nos. FERM BP-11181, FERM BP-11180 and PERM BP-11179.

Whether or not HCV of unknown genotype binds to the antibody produced by the hybridoma cell line having accession No. FERM BP-11181, FERM BP-11180, FERM BP-11179, or FERM BP-11182 can be determined using any assay system without particular limitation, as long as it is capable of detecting the presence or absence of an antigen-antibody reaction. An example of such a method is an immunoassay and a Western blot method described below.

(Immunoassay)

First, a test sample containing HCV of unknown genotype is contacted with a carrier or a plate onto which the above antibody to be examined for the presence or absence of binding has been immobilized as a primary antibody and then allowed to react for a time sufficient for the formation of an antibody-antigen complex under conditions of 4° C.-37° C.

Next, a secondary antibody labeled with an enzyme, a dye, a radioisotope, or the like, which binds to HCV in a non-genotype-specific manner, is contacted with the antibody-antigen complex and then allowed to react for a time sufficient for the formation of an antibody-antigen-secondary antibody complex under conditions of 4° C.-37° C.

Finally, the presence or absence of the thus formed antibody-antigen-secondary antibody complex is detected using as an indicator signals from the enzyme, dye, or radioisotope used for labeling the secondary antibody, so that the presence or absence of binding with the above antibodies can be determined.

(Western Blot Method)

First, a test sample containing HCV of unknown genotype is spotted onto a membrane such as a nitrocellulose membrane or a PVDF membrane and then proteins contained in the test sample are immobilized.

Next, the membrane is soaked in 5% skim milk, 1% BSA solution, or a commercial blocking agent for blocking, sufficiently washed with buffer, and then transferred into buffer containing the above antibody labeled with an enzyme, a dye, a radioisotope, or the like to be examined for the presence or absence of binding. A reaction is carried out for a time sufficient for the formation of an antibody-antigen complex under conditions of 4° C.-37° C.

Subsequently, the membrane is sufficiently washed and then signals from the enzyme, dye, or radioisotope used for labeling the above antibody for examination of the presence or absence of binding are detected, so that the presence or absence of binding with the above antibody is determined.

All publications, patents, and patent applications cited herein are incorporated herein by reference in their entirety.

EXAMPLES

The present invention will be explained more specifically with reference to the following examples. However, these examples are only illustrative, and the scope of the present invention is not limited to these examples.

Example 1

Preparation of Vector for Expression of Fusion Protein of Antigen E2 Protein of HCV Strain and Labeling Protein (1) Construction of Vector for Expression of Fusion Protein of Antigen E2 Protein Derived from J6CF Strain of HCV2a and 3xFlag Tag The antigen E2 protein derived from the J6CF strain of HCV2a; that is, a protein consisting of the region without transmembrane region of the E2 protein of the J6CF strain of HCV2a, was prepared as described below.

First, a gene encoding a protein consisting of a region corresponding to amino acid positions 384 to 720 of the precursor protein (SEQ ID NO: 5) of the J6CF strain, when the initiation methionine at the N-terminus was determined to be the $1^{st}$ amino acid, was amplified by a PCR method using the cDNA of the genomic RNA of the J6CF strain of HCV2a (GenBank Accession No. AF177036) as a template, an Advantage GC2 PCR kit (Takara Bio Inc.), and J6E2dTM-s (SEQ ID NO: 6: CACAAGCTTCGCACCCATACTGT-TGGGG) and J6E2dTM-as (SEQ ID NO: 7: GCTCTAGAT-TACCATCGGACGATGTATTTTGT) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and BamH I and thus excised from clones having the correct nucleotide sequence insert. The gene fragment was inserted in-frame between Hind III and BamH I sites of p3xFLAG-CMV-9 (Sigma) such that the reading frames matched. As a result, a CMV-3xFLAGJ6E2dTM vector expressing the antigen E2 protein to which 3xFLAG-tag had been connected (hereinafter, 3xFLAG-J6E2dTM protein) was obtained.

(2) Construction of Vector for Expression of Fusion Protein of Antigen E2 Protein Derived from J6CF Strain of HCV2a and Human IgG Fc Protein Added to the Antigen E2 Protein First, a gene encoding a protein consisting of the region corresponding to amino acid positions 384 to 720 of the precursor protein (SEQ ID NO: 5) of the J6CF strain, when the initiation methionine at the N-terminus was determined to be the $1^{st}$ amino acid, was amplified by a PCR method using the genomic RNA of the cDNA of the J6CF strain of HCV2a (GenBank Accession No. AF177036) as a template, an Advantage GC2 PCR kit (Takara Bio Inc.), and J6E2Fc-s (SEQ ID NO: 8: CACAAGCTTCGCACCCATACTGT-TGGGG) and J6E2Fc-as (SEQ ID NO: 9: ACAGGATC-CCATCGGACGATGTATTTTGTG) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and BamH I and thus excised from clones having the correct nucleotide sequence insert. The gene fragment was inserted between the Hind III site and the BamH I site downstream of the signal peptide sequence of p3xFLAG-CMV-13 (Sigma) such that the reading frames (readable frame) matched, that is, inserted in-frame. The resulting vector was designated as CMV-13-J6E2.

Subsequently, CMV-13-J6E2 was digested with Sac I and BamH I. DNA fragments encoding the signal peptide sequence and the antigen E2 protein, respectively, were each separated by agarose gel electrophoresis, and then purified using GeneElute (Sigma).

Thereafter, DNA fragments encoding the above signal peptide sequence and the antigen E2 protein, respectively, were inserted in-frame (so that the reading frames matched) between the Sac I site and the BamH I site of the CDM-mIL7R-Ig vector (Sudo et al., Proc Natl. Acad Sci U.S.A., 1993, Vol. 90, p. 9125-9129) expressing a chimeric protein comprising mouse IL-7 receptor-human immunoglobulin Fc domain. Thus, a CDM-J6E2Fc vector expressing the antigen E2 protein to which the human immunoglobulin Fc domain had been connected (hereinafter, J6E2-Fc protein) was obtained.

(3) Construction of Vector for Expression of Fusion Protein of Antigen E2 Protein Derived from JFH1 Strain of HCV2a and Human IgG Fc Protein First, a gene encoding a protein consisting of the region corresponding to amino acid positions 384 to 721 of a precursor protein of the JFH1 strain, when the initiation methionine at the N-terminus was determined to be the $1^{st}$ amino acid, was amplified by a PCR method using as a template the cDNA of the genomic RNA of the JFH1 strain of HCV2a (GenBank Accession No. AB047639), an Advantage GC2 PCR kit (Takara Bio Inc.), and JFE2Fc-s (SEQ ID NO: 10: CACAAGCTTGGCACCACCACCGTTGGAG) and JFE2Fc-as (SEQ ID NO: 11: ACAGGATCCTCCCATC-GAACGACGTATTTTGTG) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and BamH I and thus excised from clones having the correct nucleotide sequence insert and then inserted in-frame between the Hind III site and the BamH I site downstream of a signal peptide sequence of p3xFLAG-CMV-13 (Sigma). The vector was designated as CMV-13-JFH1E2.

Subsequently, CMV-13-JFH1E2 was digested with Sac I and BamH I. DNA fragments encoding the signal peptide sequence and the antigen E2 protein, respectively, were each separated by agarose gel electrophoresis, and then purified using GeneElute (Sigma).

Thereafter, DNA fragments encoding the above signal peptide sequence and the antigen E2 protein, respectively, were inserted in-frame between the Sac I site and the BamH I site of CDM-mIL7R-Ig. Thus a CDM-JFH1E2Fc vector expressing the antigen E2 protein to which the human immunoglobulin Fc domain had been connected (hereinafter, JFH1E2-Fc protein) was obtained.

(4) Construction of Vector for Expression of Fusion Protein of Antigen E2 Protein Derived from TH Strain of HCV1b and Human IgG Fc Protein First, a gene encoding a protein consisting of the region corresponding to amino acid positions 384 to 717 of a precursor protein of the TH strain, when the initiation methionine at the N-terminus was determined to be the $1^{st}$ amino acid, was amplified by a PCR method using as a template the cDNA of the genomic RNA of the TH strain of HCV1b (International Patent Publication WO2006/022422), an Advantage GC2 PCR kit (Takara Bio Inc.), and THE2Fc-s (SEQ ID NO: 12: CAAAGCTTGCGACCTACGT GACGGGGGGGTCG) and THE2Fc-as (SEQ ID NO: 13: CCTCTAGATTAT GGATCCCATTTGATTGCATAGGAGACAACCG) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and BamH I and thus excised from clones having the correct nucleotide sequence insert. The gene fragment was inserted in-frame between the Hind III site and the BamH I site downstream of a signal peptide sequence of p3xFLAG-CMV-13 (Sigma). The vector was designated as CMV-13-THE2.

Subsequently, CMV-13-THE2 was digested with Sac I and BamH I. DNA fragments encoding the signal peptide sequence and the antigen E2 protein, respectively, were each separated by agarose gel electrophoresis and then purified using GeneElute (Sigma).

Thereafter, DNA fragments encoding the signal peptide sequence and the antigen E2 protein, respectively, were inserted in-frame between the Sac I site and the BamH I site of CDM-mIL7R-Ig. Thus, a CDM-THE2Fc vector expressing the antigen E2 protein to which the human immunoglobulin Fc domain had been connected (hereinafter, THE2-Fc protein) was obtained.

(5) Construction of Vector for Expression of Fusion Protein of Antigen E2 Protein Derived from Con1 Strain of HCV1b and Human IgG Fc Protein First, a gene encoding a protein consisting of the region corresponding to amino acid positions 384 to 716 of a precursor protein of the Co n1 strain, when the initiation methionine at the N-terminus was determined to be the $1^{st}$ amino acid, was amplified by a PCR method using as a template the cDNA of the genomic RNA of the Con1 strain of HCV1b (GenBank Accession No. AJ238799), an Advantage GC2 PCR kit (Takara Bio Inc.), and Con1E2Fc-s (SEQ ID NO: 14: CAAAGCTTGGAACCTATGTGACA GGGGGGACGAT) and Con1E2Fc-as (SEQ ID NO: 15: CCTCTAGATTATG GATCCCATTTGATTGCAAAGGAGACAAC) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and BamH I and thus excised from clones having the correct nucleotide sequence insert. The gene fragment was inserted in-frame between the Hind III site and the BamH I site downstream of a signal peptide sequence of p3xFLAG-CMV-13 (Sigma). The vector was designated as CMV-13-Con1E2.

Subsequently, CMV-13-Con1E2 was digested with Sac I and BamH I. DNA fragments encoding the signal peptide sequence and the antigen E2 protein, respectively, were each separated by agarose gel electrophoresis and then purified using GeneElute (Sigma).

Thereafter, DNA fragments encoding the signal peptide sequence and the antigen E2 protein, respectively, were inserted in-frame between the Sac I site and the BamH I site of CDM-mIL7R-Ig. Thus, a CDM-Con1E2Fc vector expressing the antigen E2 protein to which the human immunoglobulin Fc domain had been connected (hereinafter, Con1E2-Fc protein) was obtained.

(6) Construction of Vector for Expression of Fusion Protein of Antigen E2 Protein Derived from J1 Strain of HCV1b and Human IgG Fc Protein First, a gene encoding a protein consisting of the region corresponding to amino acid positions 384 to 716 of a precursor protein of the J1 strain, when the initiation methionine at the N-terminus was determined to be the $1^{st}$ amino acid, was amplified by a PCR method using as a template the cDNA of genomic RNA derived from the J1 strain of HCV1b (Gen Bank Accession No. D89815), an Advantage GC2 PCR kit (Takara Bio Inc.), and J1E2Fc-s (SEQ ID NO: 16: CAAAGCTTCATACCCGCGTGACGGG GGGGGTGC) and J1E2Fc-as (SEQ ID NO: 17: CCTCTAGATTATGGATCC CACTTGATGGCAATGGAGACGACC) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and BamH I and thus excised from clones having the correct nucleotide sequence insert. The gene fragment was inserted in-frame between the Hind III site and the BamH I site downstream of the signal peptide sequence of p3xFLAG-CMV-13 (Sigma). The vector was designated as CMV-13-J1E2.

Subsequently, CMV-13-J1E2 was digested with Tth111 I, blunt-ended with T4 DNA polymerase, and then digested with BamH I. The resulting DNA fragments encoding the signal peptide sequence and the antigen E2 protein, respectively, were each separated by agarose gel electrophoresis and then purified using GeneElute (Sigma).

Thereafter, CDM-mILR7R-Ig was digested with BamH I and Xba I to excise a DNA fragment containing the sequence encoding human immunoglobulin Fc domain. And then the fragment was inserted downstream of a promoter region in pcDL-SRα296 (Takebe et al., Proc Natil Acad Sci. U.S.A., 1987, Vol. 84, p. 7388-7392) to prepare SRαIgG1Fc. Furthermore, DNA fragments encoding the signal peptide sequence and the antigen E2 protein, respectively, were inserted in-frame between the EcoR V site and the BamH I site in SRαIgG1Fc. Thus, an SRα-J1E2Fc vector expressing the antigen E2 protein to which the human immunoglobulin Fc domain had been connected (hereinafter, J1E2-Fc protein) was obtained.

(7) Construction of Vector for Expression of Fusion Protein of Antigen E2 Protein Derived from H77 Strain of HCV1a and Human IgG Fc Protein First, a gene encoding a protein consisting of the region corresponding to amino acid positions 384 to 716 of a precursor protein of the H77 strain, when the initiation methionine at the N-terminus was determined to be the $1^{st}$ amino acid, was amplified by a PCR method using as a template the cDNA of the genomic RNA of the H77 strain of HCV1a (GenBank Accession No. AF011751), an Advantage GC2 PCR kit (Takara Bio Inc.), and H77E2Fc-s (SEQ ID NO: 18: CAAAGCTTGAAACCCACGTCACCGGG GGAAA) and H77E2Fc-as (SEQ ID NO: 19: CCTCTAGATTATGGATCCCA CTTAATGGCCCAGGACGCGAT) as primers.

Next, the thus amplified DNA fragment was cloned into pCR-TOPO (Invitrogen Corporation) and then 3 clones were subjected to sequence analysis. A gene fragment encoding the antigen E2 protein was digested with Hind III and Xba I and thus excised from clones having the correct nucleotide sequence insert. The gene fragment was inserted in-frame between the Hind III site and the Xba I site downstream of a signal peptide sequence of a p3xFLAG-CMV-13Xho vector which was prepared by converting the Sac I site to the Xho I site in p3xFLAG-CMV-13 (Sigma). The resulting vector was designated as CMV-13-XhoH77E2.

Subsequently, CMV-13-XhoH77E2 was digested with Xho I and BamH I and then DNA fragments encoding the signal peptide sequence and the antigen E2 protein, respectively, were each separated by agarose gel electrophoresis and then purified using GeneElute (Sigma).

Thereafter, DNA fragments encoding the signal peptide sequence and the antigen E2 protein, respectively, were inserted in-frame between the Xho I site and the BamH I site of SRα-IgG1Fc constructed in 5) above. A SRα-H77E2Fc vector expressing the antigen E2 protein to which the human immunoglobulin Fc domain had been connected (hereinafter, H77E2-Fc protein) was obtained.

Example 2

Expression of Fusion Protein of Antigen E2 Protein and Labeling protein

CMV-3xFLAGJ6E2dTM, CDM-J6E2Fc, CDM-JFH1E2Fc, CDM-THE2Fc, CDM-Con1E2Fc, SRα-J1E2Fc, and SRα-H77E2Fc constructed in Example 1 were introduced into monkey kidney-derived COS1 cells and then each fusion protein was expressed as described below.

First, COS1 cells were subcultured in RPMI1640 medium (Invitrogen Corporation) containing 10% fetal calf serum (Invitrogen Corporation), 100 U/ml penicillin, and 100 µg/ml streptomycin. On the day before the gene transfer, COS1 cells were seeded in 150 cm² culture flasks (Corning Coaster Corporation) at a split ratio of 1:2 and then cultured overnight at 37° C. in a 5% $CO_2$ incubator.

Subsequently, DEAE dextran (GE Healthcare) and chloroquine (Sigma) were added to RPMI1640 medium at final concentrations of 400 µg/ml and 100 µM, respectively. 50 µg of the above expression vector (CMV-3xFLAGJ6E2dTM, CDM-J6E2Fc, CDM-JFH1E2Fc, CDM-THE2Fc, CDM-Con1E2Fc, SRα-J1E2Fc, or SRα-H77E2Fc) was added at a concentration of 0.1 µg/µl per 13 ml and then cells were cultured for 3 to 4 days.

Thereafter, the supernatant of cultured COS1 cells was aspirated off. 10 ml of PBS(−) (Nissui Pharmaceutical Co., Ltd.) was added, and again, PBS(−) was aspirated off for washing cells. Subsequently, a DEAE dextran-DNA mixture was added at 13 ml/150 cm² flask and then the resultant was left to stand at 37° C. in the presence of 5% $CO_2$.

Four hours later, the DEAE dextran-DNA mixture was aspirated off, each flask was washed once with 10 ml of PBS, Hybridoma-SFM medium (Invitrogen Corporation) was added at 50 ml/flask, and then cells were cultured at 37° C. in the presence of 5% $CO_2$ for 4 days. Thereafter, the culture supernatant was collected in a 50-ml centrifuge tube (Corning Coaster Corporation) and then centrifuged at 2500 rpm for 30 minutes at 4° C. The supernatant was filtered through a 0.2-µm filter (Whatman).

Example 3

Purification of Fusion Protein of Antigen E2 Protein and Labeling Protein

The culture supernatant of cells into which CMV-3xFLAG-J6E2dTM had been introduced was subjected to purification using anti-FLAG M2 agarose (Sigma) as described below.

First, 1 ml of anti-FLAG M2 agarose was added to 500 ml of the culture supernatant and then allowed to react at 4° C. for 2 hours during stirring in a spinner bottle. After 2 hours, a mixture of the supernatant and anti-FLAG M2 agarose was transferred to Econocolumn (Bio-Rad Laboratories Inc.), the Void fraction was removed, and then anti-FLAG M2 agarose was collected.

Figure 4:
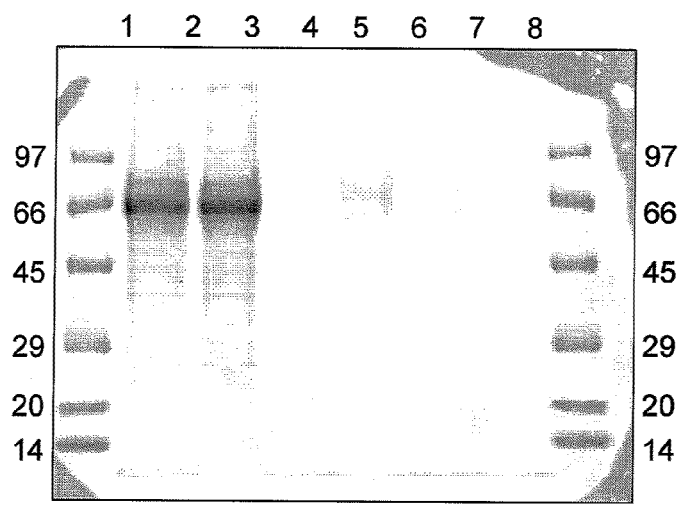

Next, anti-FLAG M2 agarose was washed twice with 10 ml of TBS (50 mM Tris-HCl, 150 mM NaCl, pH 7.4). Six fractions (anti-FLAG antibody column elution fractions 1-6) were eluted with 0.1 M Glycine-HCl (pH 3.5) to 1 ml/fraction. Immediately after elution, 1M Tris-HCl (pH 9.5) was added to return the pH to neutral. 20 µl of each fraction was fractionated under reductive conditions by SDS-polyacrylamide gel electrophoresis and then stained with Coomassie brilliant blue. As a result, it was confirmed that the fusion protein of the J6CF strain-derived antigen E2 protein and the 3xFLAG tag (3xFLAG-J6E2dTM protein) had been purified (FIG. 4).

The culture supernatant of cells into which CDM-J6E2Fc, CDM-JFH1E2Fc, CDM-THE2Fc, CDM-Con1E2Fc, SRα-J1E2Fc, or SRα-H77E2Fc had been introduced was purified using Prosep-A (Millipore) which was a carrier to which Protein-A had been bound, as described below.

First, an Econocolumn was filled with 1 ml of Prosep-A, 500 ml of the culture supernatant was caused to pass through at a flow rate of 1-1.5 mL/min, and then washed with 20 ml of PBS(−).

Figure 5:
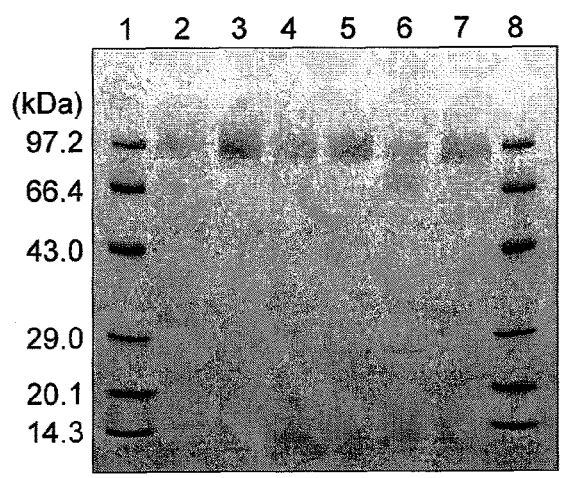

Next, 5 fractions were eluted with 0.1 M Glycine-HCl (pH 3.0) to 1 ml/fraction. Immediately after elution, 1 M Tris-HCl (pH 9.5) was added to return the pH to neutral. 20 µl of each fraction was fractionated under reductive conditions by SDS-polyacrylamide gel electrophoresis, and then stained with Coomassie brilliant blue. As a result, the fusion proteins of antigen E2 protein derived from each of the HCV strains and the human immunoglobulin Fc domain were purified and the molecular weights under reductive conditions were revealed to be about 97 kDa (FIG. 5).

Example 4

Immunization of Mouse with the Antigen E2 Protein of J6CF Strain of HCV2a 0.3 ml of a PBS solution containing 10 µg of 3xFLAG-J6E2dTM protein and 0.3 ml of Freund's complete adjuvant were mixed to prepare an emulsion. A 7-week-old Balb/c mouse (female) was subcutaneously inoculated with half the amount of the emulsion.

After 2 weeks, 0.3 ml of a PBS solution containing 10 µg of 3xFLAG-J6E2dTM protein and 0.3 ml of Freund's incomplete adjuvant were mixed to prepare an emulsion, and half the amount of the emulsion was subcutaneously administered to the mouse. After further 2 weeks, 0.15 ml of PBS solution containing 10 µg of 3xFLAG-J6E2dTM protein was administered intraperitoneally to the mouse. After 3 days, spleen cells were prepared from the mouse.

In another experiment, 0.3 ml of PBS solution containing 20 µg of the J6E2-Fc protein and 0.3 mL of Alum (Pierce) were mixed to prepare a solution to be administered. A 7-week-old Balb/c mouse (female) was inoculated intraperitoneally with the total amount of the emulsion.

At 2, 4, and 6 weeks later, similarly, 0.3 ml of PBS solution containing 20 µg of the J6E2-Fc protein and 0.3 mL of Alum were mixed to prepare a solution to be administered, and the total amount of the emulsion was administered intraperitoneally to the mouse. After further 2 months, 0.3 ml of PBS solution containing 20 µg of the J6E2-Fc protein was administered intraperitoneally to the mouse. After 3 days, spleen cells were prepared from the mouse.

Example 5

Preparation of Hybridoma Cell

First, the mouse myeloma cell line SP2/0 (obtained from ECACC) was cultured in Dulbecco's modified Eagle's medium (DMEM; Invitrogen Corporation) containing 55 µM 2-mercaptoethanol, 100 U/ml penicillin, 100 µg/ml streptomycin, and 10% fetal calf serum (FCS; Invitrogen Corporation). Thus, SP2/0 cells at the logarithmic growth phase were obtained. The cells were washed 3 times with serum-free DMEM.

Next, spleen cells were prepared from the mouse to which the 3xFLAG-J6E2dTM protein or the J6E2-Fc protein had been administered and then washed 3 times with serum-free DMEM. SP2/0 cells and mouse spleen cells were added at a ratio of 1:5 to a 50-ml centrifugal tube and then subjected to centrifugation at 1,000 rpm for 10 minutes. The supernatant was completely removed by aspiration. Subsequently, the centrifugal tube was tapped to loosen the pellet. 1 ml of 50% polyethylene glycol-1500 solution (Roche) pre-heated at 37° C. was added for 1 minute and allowed to react at 37° C. for 1 minute.

Subsequently, 1 ml of serum-free DMEM was added to the above centrifugal tube for 1 minute, and again 1 ml of serum-free DMEM was added for 1 minute, and then finally 7 ml of serum-free DMEM was added for 3 minutes, so that an ethylene glycol solution was diluted. Thereafter, the above centrifugal tube was subjected to centrifugation at 1,000 rpm for 10 minutes to collect cells. The cells were suspended at $1 \times 10^6$ cells/ml in DMEM containing 55 µM 2-mercaptoethanol, 100 U/ml penicillin, 100 µg/ml streptomycin, 15% FCS, and a 10% hybridoma cloning factor (BioVeris).

The thus obtained cell suspension was seeded at 100 µl/well in each well of a 96-well plate and then cultured at 37° C. in a 5% $CO_2$ incubator. On the next day, 100 µl of DMEM containing 2×HAT (Invitrogen Corporation), 15% FCS, and 10% hybridoma cloning factor were added to each well and then cells were continuously cultured at 37° C. in a 5% $CO_2$ incubator.

After 10 to 14 days of culture, the culture supernatant in each well was collected and then an antibody recognizing the antigen E2 protein contained in the culture supernatant was screened for as described in Example 6.

Example 6

Screening for Hybridoma Cell Producing Antibody Binding to Antigen E2 Protein

Hybridoma cells were screened for by immobilizing the antigen E2 protein on a plate and then evaluating by EIA whether or not the antibodies in the culture supernatant of hybridoma cells had bound to the antigen E2 protein immobilized on the plate.

(1) Preparation of Antigen E2 Protein-Immobilized Plate

The 3xFLAG-J6E2dTM protein or the J6E2-Fc protein was diluted to 1 µg/ml with PBS and then 50 µl each of the resultant was added to each well of an immunoplate (Nunc). The immunoplate was left to stand at 4° C. overnight, so that the protein was immobilized on the plate. The protein solution was removed from each well, 200 µl each of Blocking One solution (NACALAI TESQUE, INC.) prepared according to the included manuals was added to each well, and then blocking was carried out for 2 hours at room temperature.

(2) Screening for Hybridoma Cell

The above protein-immobilized plates subjected to blocking were used for screening for the anti-E2 protein antibody in the culture supernatant of hybridoma cells. The plate on which the J6E2-Fc protein had been immobilized was used for screening for a monoclonal antibody produced by hybridoma cells prepared from the mouse to which 3xFLAG-J6E2dTM protein had been administered. The plate on which the 3xFLAG-J6E2dTM protein had been immobilized was used for screening for a monoclonal antibody produced by hybridoma cells prepared from the mouse to which the J6E2-Fc protein had been administered.

Specifically, the above protein-immobilized plates were washed 4 times with PBS containing 0.1% Tween20 (Sigma). The supernatant sample of each hybridoma cell obtained in Example 5 was added at 50 µl/well and then allowed to react at room temperature for 1 hour. After completion of the reaction, wells were washed 4 times with PBS containing 0.1% Tween20. HRP-labeled anti-mouse IgG antibody (GE Healthcare) diluted 5,000-fold with PBS containing 0.1% Tween20 was subsequently added at 50 µl/well and allowed to react at room temperature for 1 hour. After completion of the reaction, wells were washed 4 times with PBS containing 0.1% Tween20, color was developed using a peroxidase-color-developing kit (Sumitomo Bakelite Co., Ltd.), and then absorbance at 450 nm was measured. Thus, positive clones were selected.

As a result, regarding hybridoma cells prepared from the mouse to which the 3xFLAG-J6E2dTM protein had been administered, 11 clones could be positively selected from the 980 wells subjected to screening. Cloning of these clones was carried out by limiting dilution, so that hybridoma cell lines, 1G2-32, 2F2-7, 2F3-7, 4E8-8, 5D4-6, 9G3-2, 9A5-4, 9C4-2, 8D10-3, and 10G4-1 having good proliferative property and antibody productivity were obtained.

Meanwhile, regarding hybridoma cells prepared from the mouse to which the J6E2-Fc protein had been administered, 10 clones could be positively selected from 2064 wells screened for. Cloning of these clones was carried out by limiting dilution, so that an M1E12-1 hybridoma cell line, having good proliferative property and antibody productivity was obtained.

(3) Isotype and Subtype Analysis

The isotypes and the subtypes of the monoclonal antibodies produced by the thus obtained hybridoma cells were analyzed using ImmunoPure Monoclonal Antibody Isotyping Kit (Pierce) according to the included manuals.

As a result, the antibody subtype of each clone is as shown in FIG. 6. These were all found to have x-immunoglobulin light chains.

(4) Purification of IgG Antibody

The thus obtained hybridoma cells were each finally conditioned to serum-free culture by decreasing stepwise the FCS concentration in culture medium.

Hybridoma cells were each cultured to confluence in serum-free medium, Hybridoma SFM (Invitrogen Corporation). The culture solution was collected in a centrifugation tube and then centrifuged at 1500 rpm for 5 minutes. The culture supernatant was added to Prosep-G (Millipore) and then washed with 30 bed volumes of PBS. Subsequently, 6 fractions were eluted with 1 bed volume of 0.1 M glycine-HCl (pH 3.0). Immediately after elution, 1 M Tris-HCl (pH 9.5) was added to return the pH to neutral. 20 µl of each fraction was subjected to SDS-polyacrylamide gel electrophoresis under reductive conditions and non-reductive conditions for fractionation. The presence or absence of the proteins was confirmed by staining with Coomassie brilliant blue. IgG fractions were pooled and then subjected to dialysis against PBS or demineralization through gel filtration, thereby preparing antibody samples.

Example 7

HCV Genotype Specificity of Monoclonal Antibody Against Antigen E2 Protein

It was examined whether or not the monoclonal antibody produced by each of hybridoma cells prepared via immunization with the antigen E2 protein of the J6CF strain of HCV2a had bound to E2 proteins derived from the J6CF strain of genotype 2a and the JFH1 strain of genotype 2a, E2 proteins derived from the TH strain of genotype 1b, the J1 strain of genotype 1b, and the Con1 strain of genotype 1b, and an E2 protein derived from the H77 strain of genotype 1a.

As antigens, the J6E2-Fc protein, the JFH1E2-Fc protein, the THE2-Fc protein, the J1E2-Fc protein, the Con1E2-Fc protein and the H77E2-Fc protein prepared in Examples 1-3, which are fusion proteins of the antigen E2 proteins and the human immunoglobulin Fc domains, were used. These proteins were immobilized on plates and then used for evaluation as described in Example 6.

Specifically, each of the above fusion proteins was diluted with PBS to 1 µg/ml, the diluted solution was added to an immunoplate at 50 µl/well, and then the immunoplate was left to stand at 4° C. overnight, so that each fusion protein was immobilized on the plate. The protein solution was removed and then a Blocking One solution (NACALAI TESQUE, INC.) prepared according to the included manuals was added at 200 μl/well, followed by 2 hours of blocking at room temperature.

Next, the monoclonal antibody produced by each hybridoma cell was diluted with PBS to 1 μg/ml, added to the above protein-immobilized plate at 50 μl/well, and then allowed to react at room temperature for 1 hour. After completion of the reaction, wells were washed 4 times with PBS containing 0.05% Tween20, an HRP-labeled anti-mouse IgG antibody diluted 5,000-fold with PBS containing 0.05% Tween20 was added at 50 μl/well and then allowed to react at room temperature for 1 hour. After completion of the reaction, wells were washed 4 times with PBS containing 0.05% Tween20, color was developed using a peroxidase color-developing kit, and then absorbance at 450 nm was measured.

FIG. 6 shows the binding of each monoclonal antibody to the antigen E2 proteins of various HCV genotypes or strains. Regarding absorbance values, a value of less than 0.1 is denoted with "−," a value of 0.1 or more and less than 0.25 is denoted with "+," a value of 0.25 or more and less than 0.4 is denoted with "++," and a value of 0.4 or more is denoted with "+++." These values represent the strength of binding to the antigen E2 proteins. As shown in FIG. 6, 8D10-3 was an antibody binding to the antigen E2 proteins of HCV genotypes 1a, 1b, and 2a, 1G2-32 and 2F2-7 were antibodies binding to the antigen E2 protein of genotype 2a, and 4E8-8 was an antibody binding to the antigen E2 proteins of genotypes 1b and 2a. Moreover, as shown in FIG. 6, M1E12-1 was a monoclonal antibody binding to the antigen E2 protein of the J6CF strain.

These results indicate that a set of the above monoclonal antibodies can be used for identifying HCV genotypes or HCV strains.

Also, a hybridoma cell (8D10-3) producing the monoclonal antibody 8D10-3 was deposited under accession No. FERM BP-11182, a hybridoma cell (1G2-32) producing the monoclonal antibody 1G2-32 was deposited under accession No. FERM BP-11179, a hybridoma cell (2F2-7) producing the monoclonal antibody 2F2-7 was deposited under accession No. FERM BP-11180, a hybridoma cell (4E8-8) producing the monoclonal antibody 4E8-8 was deposited under accession No. FERM BP-11181, and a hybridoma cell (M1E12-1) producing the monoclonal antibody M 1E12-1 was deposited under accession No. FERM BP-11183 on Sep. 19, 2008, with the international Patent Organisms Depositary, National Institute of Advanced Industrial Science and Technology (central 6, 1-1,Higashi 1, TsuKuba, Ibaraki, Japan).

Example 8

Analysis of Epitope for Monoclonal Antibody

A group of peptides (peptide numbers 1-110) was synthesized, each peptide having amino acid sequences of 10 contiguous amino acids which were designed to be shifted by three amino acids from the N-terminus in the amino acid sequence of antigen E2 protein corresponding to the amino acid positions 384 to 720 when the initiation methionine at the N-terminus of the precursor protein of the J6CF strain (SEQ ID NO: 5) was determined to be the $1^{st}$ amino acid. The N-terminus of each peptide was biotinylated and glycinamide was located at the C-terminus of the same (synthesized by JPT on commission).

The thus synthesized peptides were each dissolved in DMSO and then dissolved in PBS to 0.01 nmol/μl. The peptide solution was added to a streptavidin coated plate (Nunc) at 50 μl/well and then allowed to react at room temperature for 2 hours. The peptide solution was discarded, a Blocking One solution (NACALAI TESQUE, INC.) prepared according to the included manuals was added at 200 μl/well, and then wells were left to stand at 4° C. overnight, so that blocking was carried out.

Subsequently, the blocking solution was discarded, wells were washed 4 times with PBS containing 0.05% Tween20, and then each monoclonal antibody diluted to 1 μg/ml with PBS containing 0.05% Tween20 was added at 50 μl/well, followed by 1.5 hours of reaction at room temperature. After completion of the reaction, the antibody solution was discarded, wells were washed 4 times with PBS containing 0.05% Tween20, and an HRP-labeled anti-mouse IgG goat antibody (GE Healthcare) diluted 5000-fold with PBS containing 0.05% Tween20 was added at 50 μl/well and then allowed to react at room temperature for 1 hour. After the reaction, the antibody solution was discarded and then wells were washed 5 times with PBS containing 0.05% Tween20. After washing, color was developed using a peroxidase color-developing kit and then absorbance at 450 nm was measured, so that the antibody that had bound to the peptide was detected.

FIGS. 7A-E show the binding strength of each monoclonal antibody to the peptides derived from the J6CF strain-derived antigen E2 protein. A high measurement value of OD 450 nm (shown on the longitudinal axes in FIGS. 7A-E) indicates that the binding strength of the monoclonal antibody to the relevant peptide was strong and the antibody specifically recognized the peptide. Each monoclonal antibody recognized some peptides derived from the antigen E2 protein of the J6CF strain.

Figure 7:
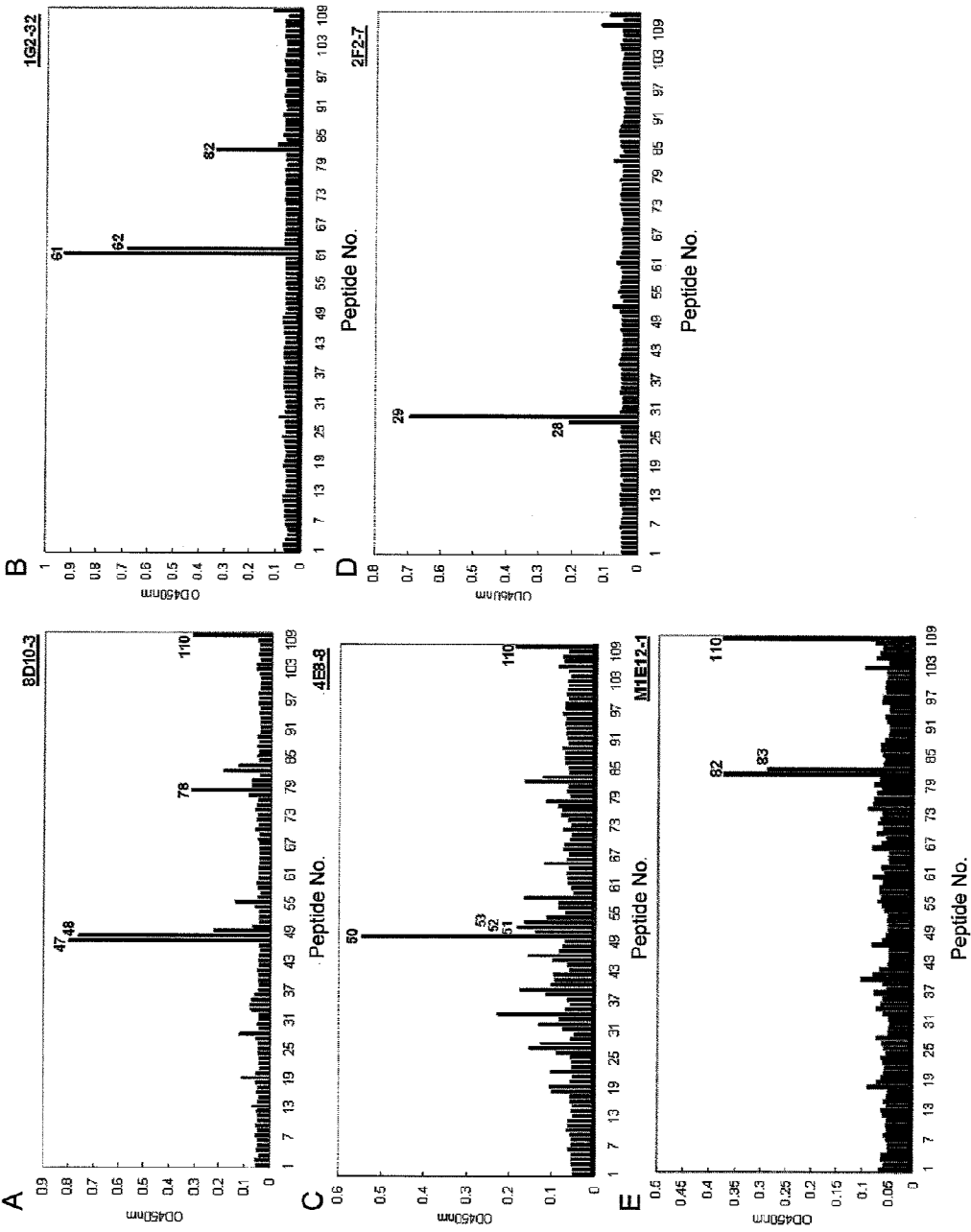
Figure 8:
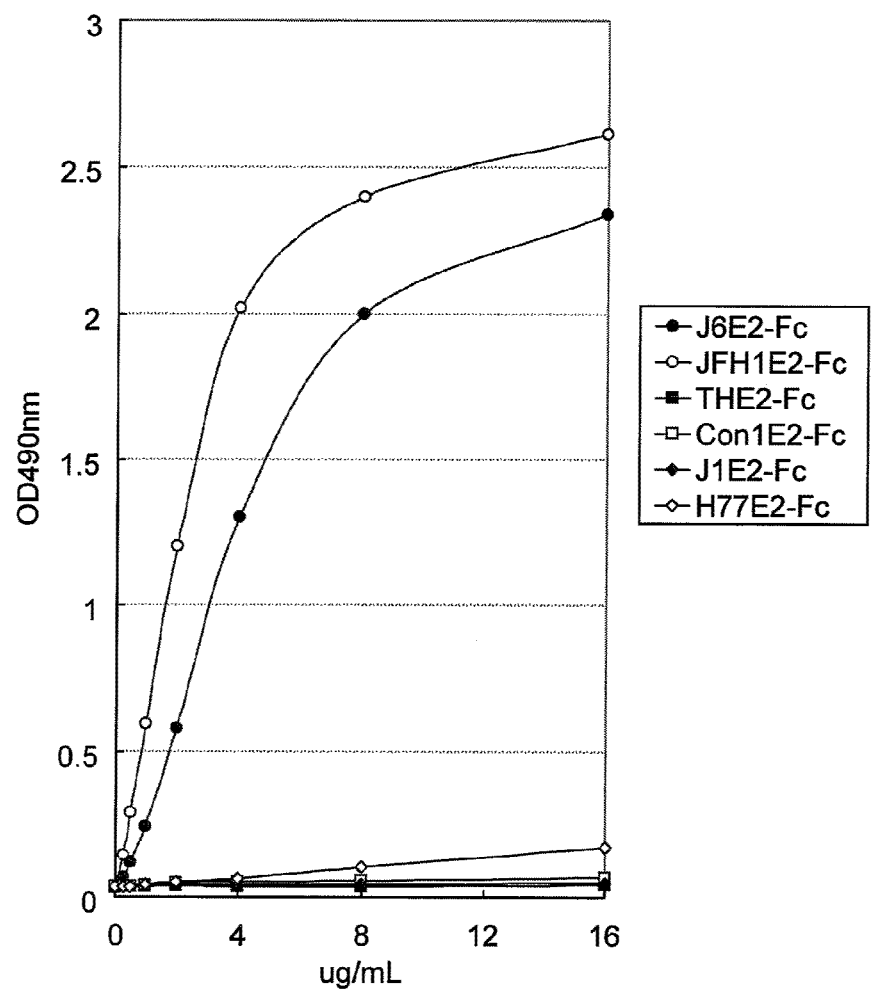
Figure 9:
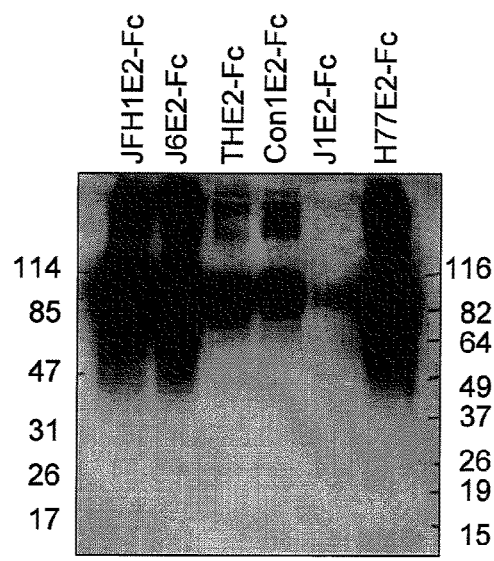

Particularly strong epitopes for the monoclonal antibody 8D10-3 were DRLGAPTYTW (SEQ ID NO: 20; peptide No. 47), and GAPTYTWGEN (SEQ ID NO: 21; peptide No. 48) overlapping with the epitope peptide (FIG. 7A). Based on the results, it was considered that the epitopes may comprise an amino acid sequence of at least 10 contiguous amino acids in the amino acid sequence DRLGAPTYTWGEN (SEQ ID NO: 22). YPYRLWHYPC (SEQ ID NO: 23; peptide No. 78) was a weak epitope (FIG. 7A).

A particularly strong epitope for the monoclonal antibody 4E8-8 was WGENETDVFL (SEQ ID NO: 1; peptide No. 50). NETDVFLLNS (SEQ ID NO: 24; peptide No. 51), DVFLLNSTRP (SEQ ID NO: 25; peptide No. 52), and LLNSTRPPLG (SEQ ID NO: 26; peptide No. 53) overlapping with the peptide No. 50 were weak epitopes (FIG. 7C). Based on the result, it was considered that each of the epitopes has an amino acid sequence of at least 10 contiguous amino acids in WGENETDVFLLNSTRPPLG (SEQ ID NO: 27).

A particularly strong epitope for the monoclonal antibody 2F2-7 was GWGALQYEDN (SEQ ID NO: 2; peptide No. 29) (FIG. 7D). FRVGWGALQY (SEQ ID NO: 28; peptide No. 28) overlapping with the peptide No. 29 was a weak epitope (FIG. 7D). Based on the result, it was considered that each of the epitopes has an amino acid sequence of at least 10 contiguous amino acids in the amino acid sequence, FRVGWGALQYEDN (SEQ ID NO: 29).

Particularly strong epitopes for the monoclonal antibody 1G2-32 were KTCGAPPCRT (SEQ ID NO: 3; peptide No. 61) and GAPPCRTRAD (SEQ ID NO: 30; peptide No. 62) (FIG. 7B). Based on the result, it was considered that each of the epitopes has an amino acid sequence of at least 10 contiguous amino acids in the amino acid sequence, KTCGAP-PCRTRAD (SEQ ID NO: 31).

Particularly strong epitopes for the monoclonal antibody M1E12-1 were NYTIFKIRMY (SEQ ID NO: 4; peptide No. 82) and IFKIRMYVGG (SEQ ID NO: 32; peptide No. 83) (FIG. 7E). Based on the results, it was considered that each of the epitopes has an amino acid sequence of at least 10 contiguous amino acids in the amino acid sequence, NYTIFKIRMYVGG (SEQ ID NO: 33).

Example 9

Detection of HCV Envelope Protein Using Monoclonal Antibody

Whether or not the antigen E2 protein derived from the H77 strain of genotype 1a, the antigen E2 proteins derived from the J6CF strain of genotype 2a and the JFH1 strain of genotype 2a, and the antigen E2 proteins derived from the TH strain of genotype 1b, the J1 strain of genotype 1b, and the Con1 strain of genotype 1b had been detected using the monoclonal antibodies prepared from the hybrdioma cells prepared above was examined by a sandwich ELISA method and a Western blot method.

(1) Sandwich ELISA

The monoclonal antibody 1G2-32 was diluted with PBS to 1 μg/ml. The antibody solution was added to an immunoplate (Nunc) at 50 μl/well, and then wells were left to stand at room temperature for 2 hours, so that the antibody was immobilized on the plate. The antibody solution was removed, a Blocking One solution (NACALAI TESQUE, INC.) prepared according to the included manuals was added at 200 μl/well, and then wells were left to stand at room temperature for 2 hours for blocking.

Next, each fusion protein of an antigen E2 protein and the human immunoglobulin Fc domain added thereto (i.e., JFH1E2-Fc protein, J6E2-Fc protein, THE2-Fc protein, Con1E2-Fc protein, J1E2-Fc protein, or H77E2-Fc protein) was diluted with PBS and then added to the above protein-immobilized plate at 50 μl/well, followed by 1.5 hours of reaction at room temperature. After completion of the reaction, wells were washed 3 times with PBS containing 0.05% Tween20. The biotinylated 8D10-3 monoclonal antibody diluted to 1 μg/ml with PBS containing 0.05% Tween20 was added at 50 μl/well and then allowed to react at room temperature for 2 hours. After the reaction, wells were washed 3 times with PBS containing 0.05% Tween20. 50 μl of HRP-labeled anti-streptavidin (GE Healthcare) diluted 5,000-fold with PBS containing 0.05% Tween20 was added and then allowed to react at room temperature for 1.5 hours.

After the reaction, wells were washed 4 times with PBS containing 0.05% Tween20, color was developed using a peroxidase color-developing kit (Sumitomo Bakelite Co., Ltd.), and then absorbance at 490 nm was measured. The results are shown in FIG. 8.

FIG. 8 shows detection sensitivity for the antigen E2 proteins of various genotypes/strains as determined by sandwich ELISA using the monoclonal antibodies 1G2-32 and 8D10-3. The horizontal axis indicates the amounts of the antigen E2 proteins and the longitudinal axis indicates absorbances at 490 nm; that is, the detected amounts of the antigen E2 proteins. The sandwich ELISA using the monoclonal antibodies 1G2-32 and 8D10-3 showed that only the antigen E2 proteins of HCV genotype 2a could be detected, and that no antigen E2 proteins of genotype 1a and genotype 1b could be detected. These results indicate that HCV genotypes or strains can be identified using the set of the antibodies obtained according to the present invention.

(2) Western Blot Method

A one-fifth volume of 5× sample buffer (0.3125 M Tris-HCl, pH 6.8, 5% SDS, 50% glycerol, 0.05% BPB, 5% 2-ME) was added to 0.1 μg to 0.3 μg of each fusion protein (JFH1E2-Fc protein, J6E2-Fc protein, THE2-Fc protein, Con1E2-Fc protein, J1E2-Fc protein, or H77E2-Fc protein) of an antigen E2 protein and the human immunoglobulin Fc domain added thereto, followed by 5 minutes of treatment at 100° C. The resultants were used as samples. Each sample was applied to 4%-20% gradient gel (TEFCO), subjected to electrophoresis with a constant current of 40 mA, and then blotted to a PVDF membrane using a semi-dry blotting apparatus at a constant current of 120 mA.

After blotting, the PVDF membrane was soaked in Block Ace (Snow Brand Milk Products Co., Ltd.) at room temperature for 1 hour for blocking, washed with TBS containing 0.1% Tween20, soaked in the 8D10-3 monoclonal antibody diluted with Can Get Signal (Toyobo Co., Ltd.) to 1 μg/mL, and then allowed to react for 1 hour at room temperature. After the reaction, the membrane was washed with TBS containing 0.1% Tween20, subsequently soaked in an HRP-labeled anti-mouse IgG antibody diluted 5,000-fold with Can Get Signal, and then allowed to react at room temperature for 1 hour. The membrane was washed with TBS containing 0.1% Tween20, and then bands were detected using an ECL kit (GE Healthcare).

FIG. 9 shows detection or lack of detection of the antigen E2 proteins of various genotypes/strains by a Western blot method using the 8D10-3 monoclonal antibody. The antigen E2 proteins of all 6 strain types could be detected with the 8D10-3 monoclonal antibody.

Industrial Applicability

The antibodies of the present invention make it possible to simply identify HCV genotypes 1a, 1b, and 2a, with high accuracy. Thus, adverse effects can be alleviated and a chance to select new therapeutic methods can be provided for hepatitis C patients infected with HCV of genotype 1a or 1b, for which no therapeutic effects of interferon therapy could previously have been expected.

The invention claimed is:

1. An antibody, which specifically binds to envelope protein 2 of hepatitis C virus of genotype 2a but does not immunologically react with envelope protein 2 of hepatitis C virus of genotype 1a, wherein said antibody is produced by the hybridoma cell line having accession No. FERM BP-11181.

2. An antibody, which specifically binds to envelope protein 2 of hepatitis C virus of genotype 2a but does not immunologically react with envelope protein 2 of hepatitis C virus of genotype 1a, and does not inummologically react with envelope protein 2 of hepatitis C virus of genotype 1b, wherein said antibody is produced by the hybridoma cell line having accession No. FERM BP-11179.

3. An antibody that specifically binds to envelope protein 2 of hepatitis C virus of genotype 2a, but does not immunologically react envelope protein 2 of hepatitis C virus of genotype 1a, and does not immunologically react with protein 2 of hepatitis C virus of genotype 1b, wherein said antibody is produced by the hybridoma cell line having accession No. FERM BP-11180.

4. An antibody that specifically binds to envelope protein 2 of hepatitis C virus of genotype 2a, but does not immunologically react with envelope protein 2 of hepatitis C virus of genotype 1a, and does not immunologically react with envelope protein 2 of hepatitis C virus of genotype 1b, wherein said antibody specifically binds to envelope protein 2 of the J6CF strain, but does not immunologically react with envelope protein 2 of the JFH1 strain, and wherein said antibody is produced by the hybridoma cell line haying accession No. FERM BP-11183.

5. A method for identifying a hepatitis C virus genotype, wherein:

the genotype of hepatitis C virus is determined to be genotype 1b if the virus binds to the antibody produced by the hybridoma cell line having accession No. FERM BP-11181, but does not bind to either of antibodies produced by the hybridoma cell lines having accession Nos. FIRM BP-11180 and FERM BP-11179;

the genotype of hepatitis C virus is determined to be genotype 2a if the virus binds to the antibody produced by the hybridoma cell line having accession No. FERM BP-11181 and binds to the antibodies produced by the hybridoma cell lines having accession Nos. FERM BP-11180 and FERM BP-11179; and the genotype of hepatitis C virus is determined to be genotype 1a if the virus binds to an antibody produced by the hybridoma cell line having accession No. FERM BP-11182, but does not bind to any of antibodies produced by the hybridoma cell lines having accession Nos. FERM BP-11181, FERM BP-11180 and FERM BP-11179.

* * * * *

SEQUENCE LISTING

```
<160> NUMBER OF SEQ ID NOS: 33

<210> SEQ ID NO 1
<211> LENGTH: 10
<212> TYPE: PRT
<213> ORGANISM: Hepatitis C virus

<400> SEQUENCE: 1
```

```
Trp Gly Glu Asn Glu Thr Asp Val Phe Leu
1               5                   10

<210> SEQ ID NO 2
<211> LENGTH: 10
<212> TYPE: PRT
<213> ORGANISM: Hepatitis C virus

<400> SEQUENCE: 2

Gly Trp Gly Ala Leu Gln Tyr Glu Asp Asn
1               5                   10

<210> SEQ ID NO 3
<211> LENGTH: 10
<212> TYPE: PRT
<213> ORGANISM: Hepatitis C virus

<400> SEQUENCE: 3

Lys Thr Cys Gly Ala Pro Pro Cys Arg Thr
1               5                   10

<210> SEQ ID NO 4
<211> LENGTH: 10
<212> TYPE: PRT
<213> ORGANISM: Hepatitis C virus

<400> SEQUENCE: 4

Asn Tyr Thr Ile Phe Lys Ile Arg Met Tyr
1               5                   10

<210> SEQ ID NO 5
<211> LENGTH: 3033
<212> TYPE: PRT
<213> ORGANISM: Hepatitis C virus

<400> SEQUENCE: 5

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
```

```
            180                 185                 190
Glu Val Lys Asn Ile Ser Thr Gly Tyr Met Val Thr Asn Asp Cys Thr
            195                 200                 205

Asn Asp Ser Ile Thr Trp Gln Leu Gln Ala Val Leu His Val Pro
    210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
        355                 360                 365

Ala Lys Val Val Ile Leu Leu Leu Ala Ala Gly Val Asp Ala Arg
    370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ser Leu Phe Tyr Thr His Ser Phe Asn
        435                 440                 445

Ser Ser Gly Cys Pro Glu Arg Met Ser Ala Cys Arg Ser Ile Glu Ala
    450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Arg Gln Cys
                485                 490                 495

Gly Val Val Ser Ala Lys Thr Val Cys Gly Pro Val Tyr Cys Phe Thr
            500                 505                 510

Pro Ser Pro Val Val Gly Thr Thr Asp Arg Leu Gly Ala Pro Thr
        515                 520                 525

Tyr Thr Trp Gly Glu Asn Glu Thr Asp Val Phe Leu Leu Asn Ser Thr
    530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
        595                 600                 605
```

```
Pro Arg Cys Leu Ile Asp Tyr Pro Tyr Arg Leu Trp His Tyr Pro Cys
    610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                    645                 650                 655

Asn Leu Glu Asp Arg Asp Arg Ser Gln Leu Ser Pro Leu Leu His Ser
                660                 665                 670

Thr Thr Glu Trp Ala Ile Leu Pro Cys Ser Tyr Ser Asp Leu Pro Ala
            675                 680                 685

Leu Ser Thr Gly Leu Leu His Leu His Gln Asn Ile Val Asp Val Gln
690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Ala Asp Ala Arg Val Cys
                725                 730                 735

Ala Cys Leu Trp Met Leu Ile Leu Leu Gly Gln Ala Glu Ala Ala Leu
                740                 745                 750

Glu Lys Leu Val Ile Leu His Ala Ala Ser Ala Ala Ser Cys Asn Gly
            755                 760                 765

Phe Leu Tyr Phe Val Ile Phe Phe Val Ala Ala Trp Tyr Ile Lys Gly
770                 775                 780

Arg Val Val Pro Leu Ala Thr Tyr Ser Leu Thr Gly Leu Trp Ser Phe
785                 790                 795                 800

Ser Leu Leu Leu Leu Ala Leu Pro Gln Gln Ala Tyr Ala Tyr Asp Ala
                805                 810                 815

Ser Val His Gly Gln Ile Gly Ala Ala Leu Leu Val Met Ile Thr Leu
            820                 825                 830

Phe Thr Leu Thr Pro Gly Tyr Lys Thr Leu Leu Ser Arg Phe Leu Trp
                835                 840                 845

Trp Leu Cys Tyr Leu Leu Thr Leu Gly Glu Ala Met Val Gln Glu Trp
    850                 855                 860

Ala Pro Pro Met Gln Val Arg Gly Gly Arg Asp Gly Ile Ile Trp Ala
865                 870                 875                 880

Val Ala Ile Phe Tyr Pro Gly Val Val Phe Asp Ile Thr Lys Trp Leu
                885                 890                 895

Leu Ala Val Leu Gly Pro Ala Tyr Leu Leu Lys Gly Ala Leu Thr Arg
                900                 905                 910

Val Pro Tyr Phe Val Arg Ala His Ala Leu Leu Arg Met Cys Thr Met
            915                 920                 925

Ala Arg His Leu Ala Gly Gly Arg Tyr Val Gln Met Ala Leu Leu Ala
930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
                980                 985                 990

Glu Thr Ala Ala Cys Gly Asp Ile Leu His Gly Leu Pro Val Ser Ala
            995                 1000                1005

Arg Leu Gly Arg Glu Val Leu Leu Gly Pro Ala Asp Gly Tyr Thr
    1010                1015                1020
```

```
Ser Lys Gly Trp Ser Leu Leu Ala Pro Ile Thr Ala Tyr Ala Gln
    1025                1030                1035

Gln Thr Arg Gly Leu Leu Gly Thr Ile Val Val Ser Met Thr Gly
    1040                1045                1050

Arg Asp Lys Thr Glu Gln Ala Gly Glu Ile Gln Val Leu Ser Thr
    1055                1060                1065

Val Thr Gln Ser Phe Leu Gly Thr Ser Ile Ser Gly Val Leu Trp
    1070                1075                1080

Thr Val Tyr His Gly Ala Gly Asn Lys Thr Leu Ala Gly Ser Arg
    1085                1090                1095

Gly Pro Val Thr Gln Met Tyr Ser Ser Ala Glu Gly Asp Leu Val
    1100                1105                1110

Gly Trp Pro Ser Pro Gly Thr Lys Ser Leu Glu Pro Cys Thr
    1115                1120                1125

Cys Gly Ala Val Asp Leu Tyr Leu Val Thr Arg Asn Ala Asp Val
    1130                1135                1140

Ile Pro Ala Arg Arg Gly Asp Lys Arg Gly Ala Leu Leu Ser
    1145                1150                1155

Pro Arg Pro Leu Ser Thr Leu Lys Gly Ser Ser Gly Gly Pro Val
    1160                1165                1170

Leu Cys Pro Arg Gly His Ala Val Gly Val Phe Arg Ala Ala Val
    1175                1180                1185

Cys Ser Arg Gly Val Ala Lys Ser Ile Asp Phe Ile Pro Val Glu
    1190                1195                1200

Thr Leu Asp Ile Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala
    1250                1255                1260

Ala Thr Leu Gly Phe Gly Ala Tyr Leu Ser Lys Ala His Gly Ile
    1265                1270                1275

Asn Pro Asn Ile Arg Thr Gly Val Arg Thr Val Thr Thr Gly Ala
    1280                1285                1290

Pro Ile Thr Tyr Ser Thr Tyr Gly Lys Phe Leu Ala Asp Gly Gly
    1295                1300                1305

Cys Ala Gly Gly Ala Tyr Asp Ile Ile Ile Cys Asp Glu Cys His
    1310                1315                1320

Ala Val Asp Ser Thr Thr Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350

Thr Pro Pro Gly Ser Val Thr Thr Pro His Pro Asn Ile Glu Glu
    1355                1360                1365

Val Ala Leu Gly Gln Glu Gly Glu Ile Pro Phe Tyr Gly Arg Ala
    1370                1375                1380

Ile Pro Leu Ser Tyr Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Leu Asn Ser Val Ala Tyr Tyr Arg Gly Leu Asp Val Ser
```

-continued

```
              1415                1420                1425
Val Ile Pro Thr Gln Gly Asp Val Val Val Ala Thr Asp Ala
              1430                1435                1440
Leu Met Thr Gly Tyr Thr Gly Asp Phe Asp Ser Val Ile Asp Cys
              1445                1450                1455
Asn Val Ala Val Thr Gln Val Val Asp Phe Ser Leu Asp Pro Thr
              1460                1465                1470
Phe Thr Ile Thr Thr Gln Ile Val Pro Gln Asp Ala Val Ser Arg
              1475                1480                1485
Ser Gln Arg Arg Gly Arg Thr Gly Arg Gly Arg Leu Gly Ile Tyr
              1490                1495                1500
Arg Tyr Val Ser Thr Gly Glu Arg Ala Ser Gly Met Phe Asp Ser
              1505                1510                1515
Val Val Leu Cys Glu Cys Tyr Asp Ala Gly Ala Ala Trp Tyr Glu
              1520                1525                1530
Leu Thr Pro Ser Glu Thr Thr Val Arg Leu Arg Ala Tyr Phe Asn
              1535                1540                1545
Thr Pro Gly Leu Pro Val Cys Gln Asp His Leu Glu Phe Trp Glu
              1550                1555                1560
Ala Val Phe Thr Gly Leu Thr His Ile Asp Ala His Phe Leu Ser
              1565                1570                1575
Gln Thr Lys Gln Ser Gly Glu Asn Phe Ala Tyr Leu Thr Ala Tyr
              1580                1585                1590
Gln Ala Thr Val Cys Ala Arg Ala Lys Ala Pro Pro Pro Ser Trp
              1595                1600                1605
Asp Val Met Trp Lys Cys Leu Thr Arg Leu Lys Pro Thr Leu Val
              1610                1615                1620
Gly Pro Thr Pro Leu Leu Tyr Arg Leu Gly Ser Val Thr Asn Glu
              1625                1630                1635
Val Thr Leu Thr His Pro Val Thr Lys Tyr Ile Ala Thr Cys Met
              1640                1645                1650
Gln Ala Asp Leu Glu Val Met Thr Ser Thr Trp Val Leu Ala Gly
              1655                1660                1665
Gly Val Leu Ala Ala Val Ala Ala Tyr Cys Leu Ala Thr Gly Cys
              1670                1675                1680
Val Cys Ile Ile Gly Arg Leu His Ile Asn Gln Arg Ala Val Val
              1685                1690                1695
Ala Pro Asp Lys Glu Val Leu Tyr Glu Ala Phe Asp Glu Met Glu
              1700                1705                1710
Glu Cys Ala Ser Arg Ala Ala Leu Ile Glu Glu Gly Gln Arg Ile
              1715                1720                1725
Ala Glu Met Leu Lys Ser Lys Ile Gln Gly Leu Leu Gln Gln Ala
              1730                1735                1740
Ser Lys Gln Ala Gln Asp Ile Gln Pro Thr Val Gln Ala Ser Trp
              1745                1750                1755
Pro Lys Val Glu Gln Phe Trp Ala Lys His Met Trp Asn Phe Ile
              1760                1765                1770
Ser Gly Ile Gln Tyr Leu Ala Gly Leu Ser Thr Leu Pro Gly Asn
              1775                1780                1785
Pro Ala Val Ala Ser Met Met Ala Phe Ser Ala Ala Leu Thr Ser
              1790                1795                1800
Pro Leu Ser Thr Ser Thr Thr Ile Leu Leu Asn Ile Leu Gly Gly
              1805                1810                1815
```

```
Trp Leu Ala Ser Gln Ile Ala Pro Pro Ala Gly Ala Thr Gly Phe
    1820            1825            1830

Val Val Ser Gly Leu Val Gly Ala Ala Val Gly Ser Ile Gly Leu
    1835            1840            1845

Gly Lys Val Leu Val Asp Ile Leu Ala Gly Tyr Gly Ala Gly Ile
    1850            1855            1860

Ser Gly Ala Leu Val Ala Phe Lys Ile Met Ser Gly Glu Lys Pro
    1865            1870            1875

Ser Met Glu Asp Val Val Asn Leu Leu Pro Gly Ile Leu Ser Pro
    1880            1885            1890

Gly Ala Leu Val Val Gly Val Ile Cys Ala Ala Ile Leu Arg Arg
    1895            1900            1905

His Val Gly Pro Gly Glu Gly Ala Val Gln Trp Met Asn Arg Leu
    1910            1915            1920

Ile Ala Phe Ala Ser Arg Gly Asn His Val Ala Pro Thr His Tyr
    1925            1930            1935

Val Thr Glu Ser Asp Ala Ser Gln Arg Val Thr Gln Leu Leu Gly
    1940            1945            1950

Ser Leu Thr Ile Thr Ser Leu Leu Arg Arg Leu His Asn Trp Ile
    1955            1960            1965

Thr Glu Asp Cys Pro Ile Pro Cys Gly Gly Ser Trp Leu Arg Asp
    1970            1975            1980

Val Trp Asp Trp Val Cys Thr Ile Leu Thr Asp Phe Lys Asn Trp
    1985            1990            1995

Leu Thr Ser Lys Leu Phe Pro Lys Met Pro Gly Leu Pro Phe Val
    2000            2005            2010

Ser Cys Gln Lys Gly Tyr Lys Gly Val Trp Ala Gly Thr Gly Ile
    2015            2020            2025

Met Thr Thr Arg Cys Pro Cys Gly Ala Asn Ile Ser Gly Asn Val
    2030            2035            2040

Arg Leu Gly Ser Met Arg Ile Thr Gly Pro Lys Thr Cys Met Asn
    2045            2050            2055

Ile Trp Gln Gly Thr Phe Pro Ile Asn Cys Tyr Thr Glu Gly Gln
    2060            2065            2070

Cys Val Pro Lys Pro Ala Pro Asn Phe Lys Val Ala Ile Trp Arg
    2075            2080            2085

Val Ala Ala Ser Glu Tyr Ala Glu Val Thr Gln His Gly Ser Tyr
    2090            2095            2100

His Tyr Ile Thr Gly Leu Thr Thr Asp Asn Leu Lys Val Pro Cys
    2105            2110            2115

Gln Leu Pro Ser Pro Glu Phe Phe Ser Trp Val Asp Gly Val Gln
    2120            2125            2130

Ile His Arg Phe Ala Pro Thr Pro Lys Pro Phe Phe Arg Asp Glu
    2135            2140            2145

Val Ser Phe Cys Val Gly Leu Asn Ser Phe Val Val Gly Ser Gln
    2150            2155            2160

Leu Pro Cys Asp Pro Glu Pro Asp Thr Asp Val Leu Met Ser Met
    2165            2170            2175

Leu Thr Asp Pro Ser His Ile Thr Ala Glu Thr Ala Ala Arg Arg
    2180            2185            2190

Leu Ala Arg Gly Ser Pro Pro Ser Glu Ala Ser Ser Ser Ala Ser
    2195            2200            2205
```

-continued

```
Gln Leu Ser Ala Pro Ser Leu Arg Ala Thr Cys Thr Thr His Gly
    2210                2215                2220
Lys Ala Tyr Asp Val Asp Met Val Asp Ala Asn Leu Phe Met Gly
    2225                2230                2235
Gly Asp Val Thr Arg Ile Glu Ser Gly Ser Lys Val Val Val Leu
    2240                2245                2250
Asp Ser Leu Asp Pro Met Val Glu Glu Arg Ser Asp Leu Glu Pro
    2255                2260                2265
Ser Ile Pro Ser Glu Tyr Met Leu Pro Lys Lys Arg Phe Pro Pro
    2270                2275                2280
Ala Leu Pro Ala Trp Ala Arg Pro Asp Tyr Asn Pro Pro Leu Val
    2285                2290                2295
Glu Ser Trp Lys Arg Pro Asp Tyr Gln Pro Ala Thr Val Ala Gly
    2300                2305                2310
Cys Ala Leu Pro Pro Pro Arg Lys Thr Pro Thr Pro Pro Pro Arg
    2315                2320                2325
Arg Arg Arg Thr Val Gly Leu Ser Glu Asp Ser Ile Gly Asp Ala
    2330                2335                2340
Leu Gln Gln Leu Ala Ile Lys Ser Phe Gly Gln Pro Pro Pro Ser
    2345                2350                2355
Gly Asp Ser Gly Leu Ser Thr Gly Ala Gly Ala Ala Asp Ser Gly
    2360                2365                2370
Ser Gln Thr Pro Pro Asp Glu Leu Ala Leu Ser Glu Thr Gly Ser
    2375                2380                2385
Ile Ser Ser Met Pro Pro Leu Glu Gly Glu Leu Gly Asp Pro Asp
    2390                2395                2400
Leu Glu Pro Glu Gln Val Glu Pro Gln Pro Pro Gln Gly Gly
    2405                2410                2415
Val Ala Ala Pro Gly Ser Asp Ser Gly Ser Trp Ser Thr Cys Ser
    2420                2425                2430
Glu Glu Asp Asp Ser Val Val Cys Cys Ser Met Ser Tyr Ser Trp
    2435                2440                2445
Thr Gly Ala Leu Ile Thr Pro Cys Ser Pro Glu Glu Glu Lys Leu
    2450                2455                2460
Pro Ile Asn Pro Leu Ser Asn Ser Leu Leu Arg Tyr His Asn Lys
    2465                2470                2475
Val Tyr Cys Thr Thr Thr Lys Ser Ala Ser Leu Arg Ala Lys Lys
    2480                2485                2490
Val Thr Phe Asp Arg Met Gln Val Leu Asp Ser Tyr Tyr Asp Ser
    2495                2500                2505
Val Leu Lys Asp Ile Lys Leu Ala Ala Ser Lys Val Thr Ala Arg
    2510                2515                2520
Leu Leu Thr Met Glu Glu Ala Cys Gln Leu Thr Pro Pro His Ser
    2525                2530                2535
Ala Arg Ser Lys Tyr Gly Phe Gly Ala Lys Glu Val Arg Ser Leu
    2540                2545                2550
Ser Gly Arg Ala Val Asn His Ile Lys Ser Val Trp Lys Asp Leu
    2555                2560                2565
Leu Glu Asp Ser Glu Thr Pro Ile Pro Thr Thr Ile Met Ala Lys
    2570                2575                2580
Asn Glu Val Phe Cys Val Asp Pro Thr Lys Gly Gly Lys Lys Ala
    2585                2590                2595
Ala Arg Leu Ile Val Tyr Pro Asp Leu Gly Val Arg Val Cys Glu
```

```
                    2600                2605                2610
Lys Met Ala Leu Tyr Asp Ile Thr Gln Lys Leu Pro Gln Ala Val
    2615                2620                2625

Met Gly Ala Ser Tyr Gly Phe Gln Tyr Ser Pro Ala Gln Arg Val
    2630                2635                2640

Glu Phe Leu Leu Lys Ala Trp Ala Glu Lys Lys Asp Pro Met Gly
    2645                2650                2655

Phe Ser Tyr Asp Thr Arg Cys Phe Asp Ser Thr Val Thr Glu Arg
    2660                2665                2670

Asp Ile Arg Thr Glu Glu Ser Ile Tyr Arg Ala Cys Ser Leu Pro
    2675                2680                2685

Glu Glu Ala His Thr Ala Ile His Ser Leu Thr Glu Arg Leu Tyr
    2690                2695                2700

Val Gly Gly Pro Met Phe Asn Ser Lys Gly Gln Thr Cys Gly Tyr
    2705                2710                2715

Arg Arg Cys Arg Ala Ser Gly Val Leu Thr Thr Ser Met Gly Asn
    2720                2725                2730

Thr Ile Thr Cys Tyr Val Lys Ala Leu Ala Ala Cys Lys Ala Ala
    2735                2740                2745

Gly Ile Ile Ala Pro Thr Met Leu Val Cys Gly Asp Asp Leu Val
    2750                2755                2760

Val Ile Ser Glu Ser Gln Gly Thr Glu Glu Asp Glu Arg Asn Leu
    2765                2770                2775

Arg Ala Phe Thr Glu Ala Met Thr Arg Tyr Ser Ala Pro Pro Gly
    2780                2785                2790

Asp Pro Pro Arg Pro Glu Tyr Asp Leu Glu Leu Ile Thr Ser Cys
    2795                2800                2805

Ser Ser Asn Val Ser Val Ala Leu Gly Pro Gln Gly Arg Arg Arg
    2810                2815                2820

Tyr Tyr Leu Thr Arg Asp Pro Thr Thr Pro Ile Ala Arg Ala Ala
    2825                2830                2835

Trp Glu Thr Val Arg His Ser Pro Val Asn Ser Trp Leu Gly Asn
    2840                2845                2850

Ile Ile Gln Tyr Ala Pro Thr Ile Trp Ala Arg Met Val Leu Met
    2855                2860                2865

Thr His Phe Phe Ser Ile Leu Met Ala Gln Asp Thr Leu Asp Gln
    2870                2875                2880

Asn Leu Asn Phe Glu Met Tyr Gly Ala Val Tyr Ser Val Ser Pro
    2885                2890                2895

Leu Asp Leu Pro Ala Ile Ile Glu Arg Leu His Gly Leu Asp Ala
    2900                2905                2910

Phe Ser Leu His Thr Tyr Thr Pro His Glu Leu Thr Arg Val Ala
    2915                2920                2925

Ser Ala Leu Arg Lys Leu Gly Ala Pro Pro Leu Arg Ala Trp Lys
    2930                2935                2940

Ser Arg Ala Arg Ala Val Arg Ala Ser Leu Ile Ser Arg Gly Gly
    2945                2950                2955

Arg Ala Ala Val Cys Gly Arg Tyr Leu Phe Asn Trp Ala Val Lys
    2960                2965                2970

Thr Lys Leu Lys Leu Thr Pro Leu Pro Glu Ala Arg Leu Leu Asp
    2975                2980                2985

Leu Ser Ser Trp Phe Thr Val Gly Ala Gly Gly Gly Asp Ile Tyr
    2990                2995                3000
```

His Ser Val Ser Arg Ala Arg Pro Arg Leu Leu Leu Phe Gly Leu
    3005                3010                3015

Leu Leu Leu Phe Val Gly Val Gly Leu Phe Leu Leu Pro Ala Arg
    3020                3025                3030

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
cacaagcttc gcacccatac tgttggggg                                      28

<210> SEQ ID NO 7
<211> LENGTH: 32
<212> TYPE: DNA
<213> ORGANISM: Artificial
<220> FEATURE:
<223> OTHER INFORMATION: primer

<400> SEQUENCE: 7
gctctagatt accatcggac gatgtatttt gt                                  32

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
cacaagcttc gcacccatac tgttggggg                                      28

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
acaggatccc atcggacgat gtattttgtg                                     30

<210> SEQ ID NO 10
<211> LENGTH: 28
<212> TYPE: DNA
<213> ORGANISM: Artificial
<220> FEATURE:
<223> OTHER INFORMATION: primer

<400> SEQUENCE: 10
cacaagcttg gcaccaccac cgttggag                                       28

<210> SEQ ID NO 11
<211> LENGTH: 33
<212> TYPE: DNA
<213> ORGANISM: Artificial
<220> FEATURE:
<223> OTHER INFORMATION: primer

<400> SEQUENCE: 11
acaggatcct cccatcgaac gacgtatttt gtg                                 33

```
<210> SEQ ID NO 12
<211> LENGTH: 32
<212> TYPE: DNA
<213> ORGANISM: Artificial
<220> FEATURE:
<223> OTHER INFORMATION: primer

<400> SEQUENCE: 12
caaagcttgc gacctacgtg acgggggggt cg                           32

<210> SEQ ID NO 13
<211> LENGTH: 43
<212> TYPE: DNA
<213> ORGANISM: Artificial
<220> FEATURE:
<223> OTHER INFORMATION: primer

<400> SEQUENCE: 13
cctctagatt atggatccca tttgattgca taggagacaa ccg               43

<210> SEQ ID NO 14
<211> LENGTH: 34
<212> TYPE: DNA
<213> ORGANISM: Artificial
<220> FEATURE:
<223> OTHER INFORMATION: primer

<400> SEQUENCE: 14
caaagcttgg aacctatgtg acagggggga cgat                         34

<210> SEQ ID NO 15
<211> LENGTH: 41
<212> TYPE: DNA
<213> ORGANISM: Artificial
<220> FEATURE:
<223> OTHER INFORMATION: primer

<400> SEQUENCE: 15
cctctagatt atggatccca tttgattgca aaggagacaa c                 41

<210> SEQ ID NO 16
<211> LENGTH: 33
<212> TYPE: DNA
<213> ORGANISM: Artificial
<220> FEATURE:
<223> OTHER INFORMATION: primer

<400> SEQUENCE: 16
caaagcttca tacccgcgtg acggggggggg tgc                         33

<210> SEQ ID NO 17
<211> LENGTH: 42
<212> TYPE: DNA
<213> ORGANISM: Artificial
<220> FEATURE:
<223> OTHER INFORMATION: primer

<400> SEQUENCE: 17
cctctagatt atggatccca cttgatggca atggagacga cc                42

<210> SEQ ID NO 18
<211> LENGTH: 31
<212> TYPE: DNA
<213> ORGANISM: Artificial
<220> FEATURE:
<223> OTHER INFORMATION: primer
```

```
<400> SEQUENCE: 18
caaagcttga aacccacgtc accgggggaa a                                   31

<210> SEQ ID NO 19
<211> LENGTH: 41
<212> TYPE: DNA
<213> ORGANISM: Artificial
<220> FEATURE:
<223> OTHER INFORMATION: primer

<400> SEQUENCE: 19
cctctagatt atggatccca cttaatggcc caggacgcga t                        41

<210> SEQ ID NO 20
<211> LENGTH: 10
<212> TYPE: PRT
<213> ORGANISM: Hepatitis C virus

<400> SEQUENCE: 20

Asp Arg Leu Gly Ala Pro Thr Tyr Thr Trp
1               5                   10

<210> SEQ ID NO 21
<211> LENGTH: 10
<212> TYPE: PRT
<213> ORGANISM: Hepatitis C virus

<400> SEQUENCE: 21

Gly Ala Pro Thr Tyr Thr Trp Gly Glu Asn
1               5                   10

<210> SEQ ID NO 22
<211> LENGTH: 13
<212> TYPE: PRT
<213> ORGANISM: Hepatitis C virus

<400> SEQUENCE: 22

Asp Arg Leu Gly Ala Pro Thr Tyr Thr Trp Gly Glu Asn
1               5                   10

<210> SEQ ID NO 23
<211> LENGTH: 10
<212> TYPE: PRT
<213> ORGANISM: Hepatitis C virus

<400> SEQUENCE: 23

Tyr Pro Tyr Arg Leu Trp His Tyr Pro Cys
1               5                   10

<210> SEQ ID NO 24
<211> LENGTH: 10
<212> TYPE: PRT
<213> ORGANISM: Hepatitis C virus

<400> SEQUENCE: 24

Asn Glu Thr Asp Val Phe Leu Leu Asn Ser
1               5                   10

<210> SEQ ID NO 25
<211> LENGTH: 10
<212> TYPE: PRT
<213> ORGANISM: Hepatitis C virus

<400> SEQUENCE: 25
```

```
Asp Val Phe Leu Leu Asn Ser Thr Arg Pro
1               5                   10

<210> SEQ ID NO 26
<211> LENGTH: 10
<212> TYPE: PRT
<213> ORGANISM: Hepatitis C virus

<400> SEQUENCE: 26

Leu Leu Asn Ser Thr Arg Pro Pro Leu Gly
1               5                   10

<210> SEQ ID NO 27
<211> LENGTH: 19
<212> TYPE: PRT
<213> ORGANISM: Hepatitis C virus

<400> SEQUENCE: 27

Trp Gly Glu Asn Glu Thr Asp Val Phe Leu Leu Asn Ser Thr Arg Pro
1               5                   10                  15

Pro Leu Gly

<210> SEQ ID NO 28
<211> LENGTH: 10
<212> TYPE: PRT
<213> ORGANISM: Hepatitis C virus

<400> SEQUENCE: 28

Phe Arg Val Gly Trp Gly Ala Leu Gln Tyr
1               5                   10

<210> SEQ ID NO 29
<211> LENGTH: 13
<212> TYPE: PRT
<213> ORGANISM: Hepatitis C virus

<400> SEQUENCE: 29

Phe Arg Val Gly Trp Gly Ala Leu Gln Tyr Glu Asp Asn
1               5                   10

<210> SEQ ID NO 30
<211> LENGTH: 10
<212> TYPE: PRT
<213> ORGANISM: Hepatitis C virus

<400> SEQUENCE: 30

Gly Ala Pro Pro Cys Arg Thr Arg Ala Asp
1               5                   10

<210> SEQ ID NO 31
<211> LENGTH: 13
<212> TYPE: PRT
<213> ORGANISM: Hepatitis C virus

<400> SEQUENCE: 31

Lys Thr Cys Gly Ala Pro Pro Cys Arg Thr Arg Ala Asp
1               5                   10

<210> SEQ ID NO 32
<211> LENGTH: 10
<212> TYPE: PRT
<213> ORGANISM: Hepatitis C virus

<400> SEQUENCE: 32
```

```
Ile Phe Lys Ile Arg Met Tyr Val Gly Gly
1               5                   10

<210> SEQ ID NO 33
<211> LENGTH: 13
<212> TYPE: PRT
<213> ORGANISM: Hepatitis C virus

<400> SEQUENCE: 33

Asn Tyr Thr Ile Phe Lys Ile Arg Met Tyr Val Gly Gly
1               5                   10
```